(12) United States Patent
Wang et al.

(10) Patent No.: US 8,691,754 B2
(45) Date of Patent: *Apr. 8, 2014

(54) MICROPARTICLES WITH ENHANCED COVALENT BINDING CAPACITY AND THEIR USES

(75) Inventors: Xinwen Wang, Bedford, MA (US); Sukanta Banerjee, Pennington, NJ (US)

(73) Assignee: Bioarray Solutions, Ltd., Warren, NJ (US)

( * ) Notice: Subject to any disclaimer, the term of this patent is extended or adjusted under 35 U.S.C. 154(b) by 650 days.

This patent is subject to a terminal disclaimer.

(21) Appl. No.: 12/795,198

(22) Filed: Jun. 7, 2010

(65) Prior Publication Data

US 2010/0331213 A1    Dec. 30, 2010

Related U.S. Application Data

(63) Continuation of application No. 11/695,686, filed on Apr. 3, 2007, now Pat. No. 7,732,575, which is a continuation of application No. 10/947,095, filed on Sep. 22, 2004, now Pat. No. 7,595,279.

(60) Provisional application No. 60/504,716, filed on Sep. 22, 2003.

(51) Int. Cl.
*C07K 14/00*    (2006.01)

(52) U.S. Cl.
USPC .............................. 514/2; 530/300; 424/489

(58) Field of Classification Search
None
See application file for complete search history.

(56) References Cited

U.S. PATENT DOCUMENTS

| | | |
|---|---|---|
| 3,329,638 A | 7/1967 | Blyth |
| 3,574,614 A | 4/1971 | Carreira |
| 3,790,492 A | 2/1974 | Fulwyler |
| 3,957,741 A | 5/1976 | Rembaum et al. |
| 3,982,182 A | 9/1976 | Hogg |
| 3,989,775 A | 11/1976 | Jack et al. |
| 3,998,525 A | 12/1976 | Giglia |
| 4,003,713 A | 1/1977 | Bowser |
| 4,046,667 A | 9/1977 | Goetz |
| 4,055,799 A | 10/1977 | Coster et al. |
| 4,075,013 A | 2/1978 | Ward et al. |
| 4,102,990 A | 7/1978 | Uzgiris |
| 4,140,937 A | 2/1979 | Vecht et al. |
| 4,143,203 A | 3/1979 | Rigopulos et al. |
| 4,199,363 A | 4/1980 | Chen |
| 4,258,001 A | 3/1981 | Pierce et al. |
| 4,267,235 A | 5/1981 | Rembaum et al. |
| 4,275,053 A | 6/1981 | Rosenfield et al. |
| 4,326,008 A | 4/1982 | Rembaum |
| 4,336,173 A | 6/1982 | Ugelstad |
| 4,339,337 A | 7/1982 | Tricot et al. |
| 4,358,388 A | 11/1982 | Daniel et al. |
| 4,383,529 A | 5/1983 | Webster |
| 4,421,896 A | 12/1983 | Dorman |
| 4,456,513 A | 6/1984 | Kawai et al. |
| 4,459,378 A | 7/1984 | Ugelstad |
| 4,487,855 A | 12/1984 | Shih et al. |
| 4,497,208 A | 2/1985 | Oja et al. |
| 4,499,052 A | 2/1985 | Fulwyler |
| 4,575,407 A | 3/1986 | Diller |
| 4,591,550 A | 5/1986 | Hafeman et al. |
| 4,602,989 A | 7/1986 | Culkin |
| 4,613,559 A | 9/1986 | Ober et al. |
| 4,647,544 A | 3/1987 | Nicoli et al. |
| 4,654,267 A | 3/1987 | Ugelstad et al. |
| 4,663,408 A | 5/1987 | Schulz et al. |
| 4,665,020 A | 5/1987 | Saunders |
| 4,672,040 A | 6/1987 | Josephson |
| 4,679,439 A | 7/1987 | Culkin |
| 4,680,332 A | 7/1987 | Hair et al. |
| 4,702,598 A | 10/1987 | Böhmer |
| 4,717,655 A | 1/1988 | Fulwyler |
| 4,753,775 A | 6/1988 | Ebersole et al. |
| 4,774,189 A | 9/1988 | Schwartz |
| 4,774,265 A | 9/1988 | Ugelstad et al. |
| 4,791,310 A | 12/1988 | Honig et al. |
| 4,795,698 A | 1/1989 | Owen et al. |
| 4,806,313 A | 2/1989 | Ebersole et al. |

(Continued)

FOREIGN PATENT DOCUMENTS

| | | |
|---|---|---|
| CA | 1248873 | 1/1989 |
| DE | 4035714 | 5/1992 |

(Continued)

OTHER PUBLICATIONS

Boyd et al., "Tosyl Chloride activation of a rayon/polyester cloth for protein immobilization", Biotechnology Techniques, Apr. 1993, vol. 7, 4: 277-282.

Cosgrove et al. "A Small-angle neutron scattering study of the structure of gelatin at the surface of polystyrene latex particles". Langmuir. vol. 14: 5376-5382 (1998).

Friedli, Interaction of SWP with Bovine Serum Albumin (BSA) (Bovine Serum Albumin (BSA) and Soluble Wheat Protein (SWP) (7 pages) downloaded http://www.friedli.com/research/PhD/chapter5a.html.

Ghosh et al. "Covalent attachment of oligonucleotides to solid supports". Nucleic Acids Research. vol. 16, No. 13: 5353-5371 (1987).

Greg T. Hermanson, "Zero Length Cross-Linkers"; pp. 170-176; 429-433 (Bioconjugate Techniques; Academic Press 1996).

Hermanson, "Bioconjugate Techniques", 170-76, 430-33, 649-51, Academic Press: San Diego, (1996).

(Continued)

*Primary Examiner* — Anand Desai

(74) *Attorney, Agent, or Firm* — Womble Carlyle Sandridge & Rice, LLP

(57) ABSTRACT

A polyelectrolyte having multiple exposed functional groups, each such group being capable of covalently bonding to a molecule, is immobilized on a surface for the purpose of bonding to a biomolecule. The biomolecule can be, for example, a nucleic acid, e.g., an amine functionalized oligonucleotide. The polyelectrolyte can include, e.g., BSA (Bovine Serum Albumin) which is bound to a functionalized surface using a covalent immobilization strategy, e.g., reaction with the surface of a tosyl-activated microparticle. Following such reaction, exposed reactive functional groups on the protein, such as amine, carboxyl, thiol, hydroxyl groups can further be utilized to covalently couple the oligonucleotide of interest using suitable chemistry.

3 Claims, 8 Drawing Sheets

(56) References Cited

U.S. PATENT DOCUMENTS

| | | |
|---|---|---|
| 4,806,776 A | 2/1989 | Kley |
| 4,822,746 A | 4/1989 | Walt |
| 4,824,941 A | 4/1989 | Gordon et al. |
| 4,829,101 A | 5/1989 | Kraemer et al. |
| 4,832,814 A | 5/1989 | Root |
| 4,851,331 A | 7/1989 | Vary et al. |
| 4,873,102 A | 10/1989 | Chang et al. |
| 4,891,324 A | 1/1990 | Pease et al. |
| 4,911,806 A | 3/1990 | Hofmann |
| 4,920,056 A | 4/1990 | Dasgupta |
| 4,994,373 A | 2/1991 | Stavrianopoulos et al. |
| 4,996,265 A | 2/1991 | Okubo et al. |
| 5,002,867 A | 3/1991 | Macevicz |
| 5,015,452 A | 5/1991 | Matijevic |
| 5,028,545 A | 7/1991 | Soini |
| 5,073,498 A | 12/1991 | Schwartz et al. |
| 5,075,217 A | 12/1991 | Weber |
| 5,091,206 A | 2/1992 | Wang et al. |
| 5,105,305 A | 4/1992 | Betzig et al. |
| 5,114,864 A | 5/1992 | Walt |
| 5,126,239 A | 6/1992 | Livak et al. |
| 5,128,006 A | 7/1992 | Mitchell et al. |
| 5,132,097 A | 7/1992 | Van Deusen et al. |
| 5,132,242 A | 7/1992 | Cheung |
| 5,143,853 A | 9/1992 | Walt |
| 5,143,854 A | 9/1992 | Pirrung et al. |
| 5,147,777 A | 9/1992 | Sutton et al. |
| 5,155,044 A | 10/1992 | Ledis et al. |
| 5,173,159 A | 12/1992 | Dutertre |
| 5,185,066 A | 2/1993 | Golias |
| 5,187,096 A | 2/1993 | Giaever et al. |
| 5,194,300 A | 3/1993 | Cheung |
| 5,194,393 A | 3/1993 | Hugl et al. |
| 5,208,111 A | 5/1993 | Decher et al. |
| 5,221,417 A | 6/1993 | Basavanhally |
| 5,234,809 A | 8/1993 | Boom et al. |
| 5,241,012 A | 8/1993 | Clark |
| 5,244,630 A | 9/1993 | Khalil et al. |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,254,477 A | 10/1993 | Walt |
| 5,266,238 A | 11/1993 | Haacke et al. |
| 5,266,427 A | 11/1993 | Iwase et al. |
| 5,266,497 A | 11/1993 | Imai et al. |
| 5,281,370 A | 1/1994 | Asher et al. |
| 5,283,079 A | 2/1994 | Wang et al. |
| 5,288,577 A | 2/1994 | Yamaguchi et al. |
| 5,298,741 A | 3/1994 | Walt et al. |
| 5,301,044 A | 4/1994 | Wright |
| 5,306,618 A | 4/1994 | Prober et al. |
| 5,308,586 A | 5/1994 | Fritsche et al. |
| 5,308,749 A | 5/1994 | Sutton et al. |
| 5,320,814 A | 6/1994 | Walt et al. |
| 5,326,691 A | 7/1994 | Hozier |
| 5,326,692 A | 7/1994 | Brinkley et al. |
| 5,329,461 A | 7/1994 | Allen et al. |
| 5,348,853 A | 9/1994 | Wang et al. |
| 5,356,713 A | 10/1994 | Charmot et al. |
| 5,362,653 A | 11/1994 | Carr et al. |
| 5,364,759 A | 11/1994 | Caskey et al. |
| 5,382,512 A | 1/1995 | Smethers et al. |
| 5,382,801 A | 1/1995 | Kanayama |
| 5,389,549 A | 2/1995 | Hamaguchi et al. |
| 5,395,688 A | 3/1995 | Wang et al. |
| 5,405,784 A | 4/1995 | Van Hoegaerden |
| 5,412,087 A | 5/1995 | McGall et al. |
| 5,415,835 A | 5/1995 | Brueck et al. |
| 5,422,246 A | 6/1995 | Koopal et al. |
| 5,436,327 A | 7/1995 | Southern et al. |
| 5,442,246 A | 8/1995 | Azegami et al. |
| 5,444,330 A | 8/1995 | Leventis et al. |
| 5,447,440 A | 9/1995 | Davis et al. |
| 5,468,649 A * | 11/1995 | Shah et al. ............. 436/518 |
| 5,470,534 A | 11/1995 | Imai et al. |
| 5,474,796 A | 12/1995 | Brennan |
| 5,474,895 A | 12/1995 | Ishii et al. |
| 5,480,723 A | 1/1996 | Klainer et al. |
| 5,488,567 A | 1/1996 | Allen et al. |
| 5,496,997 A | 3/1996 | Pope |
| 5,498,392 A | 3/1996 | Wilding et al. |
| 5,510,270 A | 4/1996 | Fodor et al. |
| 5,512,157 A | 4/1996 | Guadagno et al. |
| 5,512,439 A | 4/1996 | Hornes et al. |
| 5,512,490 A | 4/1996 | Walt et al. |
| 5,514,785 A | 5/1996 | VanNess et al. |
| 5,516,635 A | 5/1996 | Ekins et al. |
| 5,518,883 A | 5/1996 | Soini |
| 5,523,231 A | 6/1996 | Reeve |
| 5,527,710 A | 6/1996 | Nacamulli et al. |
| 5,528,392 A | 6/1996 | Nakagawa et al. |
| 5,532,128 A | 7/1996 | Eggers et al. |
| 5,536,648 A | 7/1996 | Kemp et al. |
| 5,545,522 A | 8/1996 | Van Gelder et al. |
| 5,545,531 A | 8/1996 | Rava et al. |
| 5,552,086 A | 9/1996 | Siiman et al. |
| 5,552,270 A | 9/1996 | Khrapko et al. |
| 5,556,752 A | 9/1996 | Lockhart et al. |
| 5,565,324 A | 10/1996 | Still et al. |
| 5,567,304 A | 10/1996 | Datta et al. |
| 5,567,627 A | 10/1996 | Lehnen |
| 5,573,909 A | 11/1996 | Singer et al. |
| 5,582,988 A | 12/1996 | Backus et al. |
| 5,585,069 A | 12/1996 | Zanzucchi et al. |
| 5,587,128 A | 12/1996 | Wilding et al. |
| 5,593,838 A | 1/1997 | Zanzucchi et al. |
| 5,593,839 A | 1/1997 | Hubbell et al. |
| 5,602,042 A | 2/1997 | Farber |
| 5,604,097 A | 2/1997 | Brenner |
| 5,604,099 A | 2/1997 | Erlich et al. |
| 5,610,287 A | 3/1997 | Nikiforov et al. |
| 5,627,040 A | 5/1997 | Bierre et al. |
| 5,632,957 A | 5/1997 | Heller et al. |
| 5,633,724 A | 5/1997 | King et al. |
| 5,633,972 A | 5/1997 | Walt et al. |
| 5,637,508 A | 6/1997 | Kidwell et al. |
| 5,639,603 A | 6/1997 | Dower et al. |
| 5,639,606 A | 6/1997 | Wiley |
| 5,643,765 A | 7/1997 | Wiley |
| 5,648,124 A | 7/1997 | Sutor |
| 5,650,488 A | 7/1997 | O'Hare |
| 5,650,489 A | 7/1997 | Lam et al. |
| 5,652,059 A | 7/1997 | Margel |
| 5,652,107 A | 7/1997 | Lizardi et al. |
| 5,653,939 A | 8/1997 | Hollis et al. |
| 5,660,990 A | 8/1997 | Rao et al. |
| 5,667,667 A | 9/1997 | Southern |
| 5,674,686 A | 10/1997 | Schumm et al. |
| 5,674,698 A | 10/1997 | Zarling et al. |
| 5,679,524 A | 10/1997 | Nikiforov et al. |
| 5,690,894 A | 11/1997 | Pinkel et al. |
| 5,698,271 A | 12/1997 | Liberti et al. |
| 5,700,637 A | 12/1997 | Southern |
| 5,700,897 A | 12/1997 | Klainer et al. |
| 5,714,340 A | 2/1998 | Sutton et al. |
| 5,714,521 A | 2/1998 | Kedem et al. |
| 5,716,852 A | 2/1998 | Yager et al. |
| 5,722,470 A | 3/1998 | Kedar et al. |
| 5,723,218 A | 3/1998 | Haugland et al. |
| 5,723,233 A | 3/1998 | Garza et al. |
| 5,728,529 A | 3/1998 | Metzker et al. |
| 5,736,349 A | 4/1998 | Sasaki et al. |
| 5,738,986 A * | 4/1998 | Nilsson ............. 435/5 |
| 5,744,299 A | 4/1998 | Henrickson et al. |
| 5,744,305 A | 4/1998 | Fodor et al. |
| 5,747,349 A | 5/1998 | Van den Engh et al. |
| 5,751,629 A | 5/1998 | Nova et al. |
| 5,763,175 A | 6/1998 | Brenner |
| 5,763,198 A | 6/1998 | Hirth et al. |
| 5,763,263 A | 6/1998 | Dehlinger |
| 5,766,711 A | 6/1998 | Barmakian |
| 5,766,963 A | 6/1998 | Baldwin et al. |
| 5,770,358 A | 6/1998 | Dower et al. |

(56) References Cited

U.S. PATENT DOCUMENTS

| | | |
|---|---|---|
| 5,770,367 A | 6/1998 | Southern et al. |
| 5,770,455 A | 6/1998 | Cargill et al. |
| 5,770,721 A | 6/1998 | Ershov et al. |
| 5,773,222 A | 6/1998 | Scott |
| 5,776,711 A | 7/1998 | Vyas et al. |
| 5,779,976 A | 7/1998 | Leland et al. |
| 5,786,219 A | 7/1998 | Zhang et al. |
| 5,789,147 A | 8/1998 | Rubinstein et al. |
| 5,792,430 A | 8/1998 | Hamper |
| 5,800,992 A | 9/1998 | Fodor et al. |
| 5,807,755 A | 9/1998 | Ekins |
| 5,812,272 A | 9/1998 | King et al. |
| 5,814,524 A | 9/1998 | Walt et al. |
| 5,831,045 A | 11/1998 | Stolowitz et al. |
| 5,834,590 A | 11/1998 | Vinik et al. |
| 5,837,501 A | 11/1998 | Beumer et al. |
| 5,837,551 A | 11/1998 | Ekins |
| 5,837,832 A | 11/1998 | Chee et al. |
| 5,840,485 A | 11/1998 | Lebl et al. |
| 5,843,660 A | 12/1998 | Schumm et al. |
| 5,844,304 A | 12/1998 | Kata et al. |
| 5,846,708 A | 12/1998 | Hollis et al. |
| 5,855,753 A | 1/1999 | Trau et al. |
| 5,856,092 A | 1/1999 | Dale et al. |
| 5,858,804 A | 1/1999 | Zanzucchi et al. |
| 5,866,099 A | 2/1999 | Owen et al. |
| 5,866,331 A | 2/1999 | Singer et al. |
| 5,874,219 A | 2/1999 | Rava et al. |
| 5,876,946 A | 3/1999 | Burbaum et al. |
| 5,898,071 A | 4/1999 | Hawkins |
| 5,900,481 A | 5/1999 | Lough et al. |
| 5,922,617 A | 7/1999 | Wang et al. |
| 5,939,021 A | 8/1999 | Hansen et al. |
| 5,942,388 A | 8/1999 | Willner et al. |
| 5,945,525 A | 8/1999 | Uematsu et al. |
| 5,948,621 A | 9/1999 | Turner et al. |
| 5,948,627 A | 9/1999 | Lee et al. |
| 5,952,131 A | 9/1999 | Kumacheva et al. |
| 5,952,174 A | 9/1999 | Nikiforoy et al. |
| 5,959,098 A | 9/1999 | Goldberg et al. |
| 5,961,923 A | 10/1999 | Nova et al. |
| 5,965,235 A | 10/1999 | McGuire et al. |
| 5,965,452 A | 10/1999 | Kovacs |
| 5,968,736 A | 10/1999 | Still et al. |
| 5,981,176 A | 11/1999 | Wallace |
| 5,981,180 A | 11/1999 | Chandler et al. |
| 5,988,432 A | 11/1999 | Sun |
| 5,989,835 A | 11/1999 | Dunlay et al. |
| 5,993,935 A | 11/1999 | Rasmussen et al. |
| 5,994,066 A | 11/1999 | Bergeron et al. |
| 6,001,614 A | 12/1999 | Akhavan-Tafti |
| 6,004,744 A | 12/1999 | Goelet et al. |
| 6,007,996 A | 12/1999 | McNamara et al. |
| 6,013,531 A | 1/2000 | Wang et al. |
| 6,014,451 A | 1/2000 | Berry et al. |
| 6,015,664 A | 1/2000 | Henrickson et al. |
| 6,015,666 A | 1/2000 | Springer et al. |
| 6,017,696 A | 1/2000 | Heller |
| 6,018,350 A | 1/2000 | Lee et al. |
| 6,023,540 A | 2/2000 | Walt et al. |
| 6,023,590 A | 2/2000 | Abe et al. |
| 6,025,905 A | 2/2000 | Sussman |
| 6,027,889 A | 2/2000 | Barany et al. |
| 6,027,945 A | 2/2000 | Smith et al. |
| 6,033,547 A | 3/2000 | Trau et al. |
| 6,043,354 A | 3/2000 | Hillebrand et al. |
| 6,048,690 A | 4/2000 | Heller et al. |
| 6,054,270 A | 4/2000 | Southern |
| 6,060,243 A | 5/2000 | Tang et al. |
| 6,063,569 A | 5/2000 | Gildea et al. |
| 6,068,818 A | 5/2000 | Ackley et al. |
| 6,075,905 A | 6/2000 | Herman et al. |
| 6,077,669 A | 6/2000 | Little et al. |
| 6,077,674 A | 6/2000 | Schleifer et al. |
| 6,080,585 A | 6/2000 | Southern et al. |
| 6,083,699 A | 7/2000 | Leushner et al. |
| 6,083,763 A | 7/2000 | Balch |
| 6,084,991 A | 7/2000 | Sampas |
| 6,086,736 A | 7/2000 | Dasgupta et al. |
| 6,090,458 A | 7/2000 | Murakami |
| 6,090,545 A | 7/2000 | Wohlstadter et al. |
| 6,090,555 A | 7/2000 | Fiekowsky et al. |
| 6,090,912 A | 7/2000 | Lebl et al. |
| 6,096,368 A | 8/2000 | Sun |
| 6,100,030 A | 8/2000 | McCasky Feazel et al. |
| 6,103,379 A | 8/2000 | Margel et al. |
| 6,106,685 A | 8/2000 | McBride et al. |
| 6,120,666 A | 9/2000 | Jacobson et al. |
| 6,122,599 A | 9/2000 | Mehta |
| 6,123,263 A | 9/2000 | Feng |
| 6,124,092 A | 9/2000 | O'Neill et al. |
| 6,126,731 A | 10/2000 | Kemeny et al. |
| 6,130,101 A | 10/2000 | Mao et al. |
| 6,132,685 A | 10/2000 | Kercso et al. |
| 6,132,997 A | 10/2000 | Shannon |
| 6,133,436 A | 10/2000 | Koster et al. |
| 6,136,171 A | 10/2000 | Frazier et al. |
| 6,136,468 A | 10/2000 | Mitchell, Jr. et al. |
| 6,139,831 A | 10/2000 | Shivashankar et al. |
| 6,141,046 A | 10/2000 | Roth et al. |
| 6,143,499 A | 11/2000 | Mirzabekov et al. |
| 6,149,789 A | 11/2000 | Benecke et al. |
| 6,150,095 A | 11/2000 | Southern et al. |
| 6,151,062 A | 11/2000 | Inoguchi et al. |
| 6,153,375 A | 11/2000 | Kobylecki et al. |
| 6,153,389 A | 11/2000 | Haarer et al. |
| 6,156,502 A | 12/2000 | Beattie |
| 6,167,910 B1 | 1/2001 | Chow |
| 6,172,218 B1 | 1/2001 | Brenner |
| 6,180,226 B1 | 1/2001 | McArdle et al. |
| 6,183,970 B1 | 2/2001 | Okano et al. |
| 6,187,540 B1 | 2/2001 | Staub et al. |
| 6,193,866 B1 | 2/2001 | Bader et al. |
| 6,193,951 B1 | 2/2001 | Ottoboni et al. |
| 6,200,737 B1 | 3/2001 | Walt et al. |
| 6,200,814 B1 | 3/2001 | Malmqvist et al. |
| 6,203,993 B1 | 3/2001 | Shuber et al. |
| 6,207,369 B1 | 3/2001 | Wohlstadter et al. |
| 6,209,589 B1 | 4/2001 | Hare et al. |
| 6,218,111 B1 | 4/2001 | Southern et al. |
| 6,221,598 B1 | 4/2001 | Schumm et al. |
| 6,232,066 B1 | 5/2001 | Felder et al. |
| 6,235,471 B1 | 5/2001 | Knapp et al. |
| 6,238,863 B1 | 5/2001 | Schumm et al. |
| 6,245,508 B1 | 6/2001 | Heller et al. |
| 6,251,592 B1 | 6/2001 | Tang et al. |
| 6,251,595 B1 | 6/2001 | Gordon et al. |
| 6,251,687 B1 | 6/2001 | Buechler et al. |
| 6,251,691 B1 | 6/2001 | Seul |
| 6,254,754 B1 | 7/2001 | Ross et al. |
| 6,254,827 B1 | 7/2001 | Ackley et al. |
| 6,261,430 B1 | 7/2001 | Yager et al. |
| 6,261,782 B1 | 7/2001 | Lizardi et al. |
| 6,264,815 B1 | 7/2001 | Pethig et al. |
| 6,264,825 B1 | 7/2001 | Blackburn et al. |
| 6,266,459 B1 | 7/2001 | Walt et al. |
| 6,267,858 B1 | 7/2001 | Parce et al. |
| 6,268,219 B1 | 7/2001 | Mcbride et al. |
| 6,268,222 B1 | 7/2001 | Chandler et al. |
| 6,271,856 B1 | 8/2001 | Krishnamurthy |
| 6,277,579 B1 | 8/2001 | Lazar et al. |
| 6,280,618 B2 | 8/2001 | Watkins et al. |
| 6,287,778 B1 | 9/2001 | Huang et al. |
| 6,294,063 B1 | 9/2001 | Becker et al. |
| 6,297,062 B1 | 10/2001 | Gombinski |
| 6,303,316 B1 | 10/2001 | Kiel et al. |
| 6,306,643 B1 | 10/2001 | Gentalen et al. |
| 6,307,039 B1 | 10/2001 | Southern et al. |
| 6,309,602 B1 | 10/2001 | Ackley et al. |
| 6,312,134 B1 | 11/2001 | Jain et al. |
| 6,316,186 B1 | 11/2001 | Ekins |
| 6,318,970 B1 | 11/2001 | Backhouse |
| 6,319,472 B1 | 11/2001 | Ackley et al. |
| 6,319,674 B1 | 11/2001 | Fulcrand et al. |

(56) References Cited

U.S. PATENT DOCUMENTS

| | | |
|---|---|---|
| 6,321,791 B1 | 11/2001 | Chow |
| 6,327,410 B1 | 12/2001 | Walt et al. |
| 6,342,355 B1 | 1/2002 | Hacia et al. |
| 6,349,144 B1 | 2/2002 | Shams |
| 6,355,419 B1 | 3/2002 | Alfenito |
| 6,355,431 B1 | 3/2002 | Chee et al. |
| 6,355,491 B1 | 3/2002 | Zhou et al. |
| 6,358,387 B1 | 3/2002 | Kopf-Sill et al. |
| 6,361,916 B1 | 3/2002 | Chen et al. |
| 6,361,945 B1 | 3/2002 | Becker et al. |
| 6,365,418 B1 | 4/2002 | Wagner et al. |
| 6,368,799 B1 | 4/2002 | Chee |
| 6,387,707 B1 | 5/2002 | Seul et al. |
| 6,399,328 B1 | 6/2002 | Vournakis et al. |
| 6,403,309 B1 | 6/2002 | Iris et al. |
| 6,406,921 B1 | 6/2002 | Wagner et al. |
| 6,426,615 B1 | 7/2002 | Mehta |
| 6,429,027 B1 | 8/2002 | Chee et al. |
| 6,448,012 B1 | 9/2002 | Schwartz |
| 6,451,191 B1 | 9/2002 | Bentsen et al. |
| 6,458,547 B1 | 10/2002 | Bryan et al. |
| 6,468,811 B1 | 10/2002 | Seul |
| 6,480,791 B1 | 11/2002 | Strathmann |
| 6,488,872 B1 | 12/2002 | Beebe et al. |
| 6,494,924 B1 | 12/2002 | Auweter et al. |
| 6,498,863 B1 | 12/2002 | Gaidoukevitch et al. |
| 6,500,620 B2 | 12/2002 | Yu et al. |
| 6,503,680 B1 | 1/2003 | Chen et al. |
| 6,506,564 B1 | 1/2003 | Mirkin et al. |
| 6,509,158 B1 | 1/2003 | Schwartz |
| 6,514,688 B2 | 2/2003 | Muller-Schulte |
| 6,514,714 B1 | 2/2003 | Lee et al. |
| 6,514,771 B1 | 2/2003 | Seul |
| 6,515,649 B1 | 2/2003 | Albert et al. |
| 6,521,747 B2 | 2/2003 | Anastasio et al. |
| 6,528,264 B1 | 3/2003 | Pal et al. |
| 6,531,292 B1 | 3/2003 | Rine et al. |
| 6,531,323 B1 | 3/2003 | Shinoki et al. |
| 6,534,274 B2 | 3/2003 | Becker et al. |
| 6,534,293 B1 | 3/2003 | Barany et al. |
| 6,540,895 B1 | 4/2003 | Spence et al. |
| 6,605,453 B2 | 8/2003 | Ozkan et al. |
| 6,605,474 B1 | 8/2003 | Cole |
| 6,610,256 B2 | 8/2003 | Schwartz |
| 6,620,584 B1 | 9/2003 | Chee et al. |
| 6,642,062 B2 | 11/2003 | Kauver et al. |
| 6,645,432 B1 | 11/2003 | Anderson et al. |
| 6,650,703 B1 | 11/2003 | Schwarzmann et al. |
| 6,670,128 B2 | 12/2003 | Smith et al. |
| 6,692,914 B1 | 2/2004 | Klaerner et al. |
| 6,703,288 B2 | 3/2004 | Nagasawa et al. |
| 6,706,163 B2 | 3/2004 | Seul et al. |
| 6,713,309 B1 | 3/2004 | Anderson et al. |
| 6,730,515 B2 | 5/2004 | Kocher |
| 6,743,581 B1 | 6/2004 | Vo-Dinh |
| 6,760,157 B1 | 7/2004 | Allen et al. |
| 6,779,559 B2 | 8/2004 | Parce et al. |
| 6,797,524 B1 | 9/2004 | Seul |
| 6,806,050 B2 | 10/2004 | Zhou et al. |
| 6,812,005 B2 | 11/2004 | Fan et al. |
| 6,838,289 B2 | 1/2005 | Bell et al. |
| 6,844,156 B2 | 1/2005 | Rosen |
| 6,869,798 B2 | 3/2005 | Crews et al. |
| 6,881,536 B1 * | 4/2005 | Shah et al. .................. 435/5 |
| 6,887,701 B2 | 5/2005 | Anderson et al. |
| 6,890,741 B2 | 5/2005 | Fan et al. |
| 6,897,271 B1 | 5/2005 | Domschke et al. |
| 6,905,881 B2 | 6/2005 | Sammak et al. |
| 6,908,737 B2 | 6/2005 | Ravkin et al. |
| 6,942,968 B1 | 9/2005 | Dickinson et al. |
| 6,955,751 B1 | 10/2005 | Seul |
| 6,955,889 B1 | 10/2005 | Mercolino et al. |
| 6,955,902 B2 | 10/2005 | Chumakov et al. |
| 6,958,245 B2 | 10/2005 | Seul et al. |
| 6,991,941 B1 | 1/2006 | Seul |
| 6,993,156 B1 | 1/2006 | Szeliski et al. |
| 7,015,047 B2 | 3/2006 | Huang et al. |
| 7,041,453 B2 | 5/2006 | Yang |
| 7,049,077 B2 | 5/2006 | Yang |
| 7,056,746 B2 | 6/2006 | Seul et al. |
| 7,060,431 B2 | 6/2006 | Chee et al. |
| 7,090,759 B1 | 8/2006 | Seul |
| 7,097,974 B1 | 8/2006 | Stahler et al. |
| 7,099,777 B1 | 8/2006 | Ghandour |
| 7,115,884 B1 | 10/2006 | Walt et al. |
| 7,132,239 B2 | 11/2006 | Livak et al. |
| 7,141,217 B2 | 11/2006 | Karlsson et al. |
| 7,144,119 B2 | 12/2006 | Seul et al. |
| 7,157,228 B2 | 1/2007 | Hashmi et al. |
| 7,195,913 B2 | 3/2007 | Guire et al. |
| 7,229,840 B1 | 6/2007 | Wischerhoff |
| 7,262,016 B2 | 8/2007 | Huang et al. |
| 7,291,504 B2 | 11/2007 | Seul |
| 7,306,918 B2 | 12/2007 | Hashmi et al. |
| 7,320,864 B2 | 1/2008 | Yang |
| 7,335,153 B2 | 2/2008 | Seul et al. |
| 7,344,841 B2 | 3/2008 | Hashmi et al. |
| 7,358,097 B2 | 4/2008 | Seul et al. |
| 7,390,676 B2 | 6/2008 | Seul et al. |
| 7,425,416 B2 | 9/2008 | Hashmi et al. |
| 7,427,512 B2 | 9/2008 | Seul |
| 7,501,253 B2 | 3/2009 | Pourmand et al. |
| 7,526,114 B2 | 4/2009 | Xia et al. |
| 7,582,488 B2 | 9/2009 | Banerjee et al. |
| 7,595,279 B2 | 9/2009 | Wang et al. |
| 7,615,345 B2 | 11/2009 | Seul |
| 7,732,575 B2 * | 6/2010 | Wang et al. .................. 530/363 |
| 7,737,088 B1 | 6/2010 | Stahler et al. |
| 7,749,774 B2 | 7/2010 | Seul |
| 7,790,380 B2 | 9/2010 | Yang |
| 7,848,889 B2 | 12/2010 | Xia et al. |
| 7,940,968 B2 | 5/2011 | Seul et al. |
| 2001/0034614 A1 | 10/2001 | Fletcher-Haynes et al. |
| 2001/0044531 A1 | 11/2001 | McGall et al. |
| 2001/0046602 A1 | 11/2001 | Chandler et al. |
| 2001/0049095 A1 | 12/2001 | Webster |
| 2002/0006634 A1 | 1/2002 | Han et al. |
| 2002/0015952 A1 | 2/2002 | Anderson et al. |
| 2002/0022276 A1 | 2/2002 | Zhou et al. |
| 2002/0029235 A1 | 3/2002 | Lock et al. |
| 2002/0031841 A1 | 3/2002 | Asher et al. |
| 2002/0032252 A1 | 3/2002 | Ishizuka |
| 2002/0039728 A1 | 4/2002 | Kain et al. |
| 2002/0045169 A1 | 4/2002 | Shoemaker et al. |
| 2002/0081714 A1 | 6/2002 | Jain et al. |
| 2002/0102567 A1 | 8/2002 | Fodor et al. |
| 2002/0125138 A1 | 9/2002 | Medoro |
| 2002/0127603 A1 | 9/2002 | Basiji et al. |
| 2002/0137074 A1 | 9/2002 | Piunno et al. |
| 2002/0142318 A1 | 10/2002 | Cattell et al. |
| 2002/0150909 A1 | 10/2002 | Stuelpnagel et al. |
| 2002/0155481 A1 | 10/2002 | Hirota et al. |
| 2002/0166766 A1 | 11/2002 | Seul et al. |
| 2002/0182609 A1 | 12/2002 | Arcot |
| 2002/0187501 A1 | 12/2002 | Huang et al. |
| 2002/0197728 A1 | 12/2002 | Kaufman et al. |
| 2002/0198665 A1 | 12/2002 | Seul et al. |
| 2003/0003272 A1 | 1/2003 | Laguitton |
| 2003/0004594 A1 | 1/2003 | Liu et al. |
| 2003/0006143 A1 | 1/2003 | Banerjee et al. |
| 2003/0012693 A1 | 1/2003 | Otillar et al. |
| 2003/0012699 A1 | 1/2003 | Moore et al. |
| 2003/0022370 A1 | 1/2003 | Casagrande et al. |
| 2003/0022393 A1 | 1/2003 | Seul et al. |
| 2003/0031351 A1 | 2/2003 | Yim |
| 2003/0038812 A1 | 2/2003 | Bartell |
| 2003/0040129 A1 | 2/2003 | Shah |
| 2003/0062422 A1 | 4/2003 | Fateley et al. |
| 2003/0077607 A1 | 4/2003 | Hopfinger et al. |
| 2003/0082487 A1 | 5/2003 | Burgess |
| 2003/0082530 A1 | 5/2003 | Soderlund et al. |
| 2003/0082531 A1 | 5/2003 | Soderlund et al. |
| 2003/0082587 A1 | 5/2003 | Seul et al. |
| 2003/0087228 A1 | 5/2003 | Bamdad et al. |

(56) References Cited

U.S. PATENT DOCUMENTS

| | | |
|---|---|---|
| 2003/0108913 A1 | 6/2003 | Schouten |
| 2003/0129296 A1 | 7/2003 | Kelso |
| 2003/0134326 A1 | 7/2003 | Hansen et al. |
| 2003/0138842 A1 | 7/2003 | Seul et al. |
| 2003/0148335 A1 | 8/2003 | Shen et al. |
| 2003/0152931 A1 | 8/2003 | Chiou et al. |
| 2003/0154108 A1 | 8/2003 | Fletcher-Haynes et al. |
| 2003/0177036 A1 | 9/2003 | Oka et al. |
| 2003/0182068 A1 | 9/2003 | Battersby et al. |
| 2003/0186220 A1 | 10/2003 | Zhou et al. |
| 2003/0228610 A1 | 12/2003 | Seul |
| 2004/0002073 A1 | 1/2004 | Li et al. |
| 2004/0009614 A1 | 1/2004 | Ahn et al. |
| 2004/0014073 A1 | 1/2004 | Trau et al. |
| 2004/0048259 A1 | 3/2004 | Hashmi et al. |
| 2004/0093238 A1 | 5/2004 | Deakter |
| 2004/0106121 A1 | 6/2004 | Ugolin et al. |
| 2004/0132122 A1 | 7/2004 | Banerjee et al. |
| 2004/0137641 A1 | 7/2004 | Holtlund et al. |
| 2004/0175734 A1 | 9/2004 | Stahler et al. |
| 2004/0219520 A1 | 11/2004 | Mirkin et al. |
| 2004/0229269 A1 | 11/2004 | Hashmi et al. |
| 2005/0048570 A1 | 3/2005 | Weber et al. |
| 2005/0112585 A1 | 5/2005 | Zichi et al. |
| 2005/0143928 A1 | 6/2005 | Moser et al. |
| 2005/0239098 A1 | 10/2005 | Hastings et al. |
| 2006/0024732 A1 | 2/2006 | Huang et al. |
| 2006/0035240 A1 | 2/2006 | Seul et al. |
| 2006/0275799 A1 | 12/2006 | Banerjee et al. |
| 2007/0031877 A1 | 2/2007 | Stahler et al. |
| 2007/0231810 A1 | 10/2007 | Todd et al. |
| 2007/0243534 A1 | 10/2007 | Seul et al. |
| 2008/0020374 A1 | 1/2008 | Greene et al. |
| 2008/0123089 A1 | 5/2008 | Seul et al. |
| 2008/0200349 A1 | 8/2008 | Wu et al. |
| 2008/0214412 A1 | 9/2008 | Stahler et al. |
| 2008/0261205 A1 | 10/2008 | Denomme |
| 2010/0062518 A1 | 3/2010 | Banerjee |

FOREIGN PATENT DOCUMENTS

| | | |
|---|---|---|
| EP | 0126450 | 11/1984 |
| EP | 179039 | 4/1986 |
| EP | 246864 | 11/1987 |
| EP | 269764 | 6/1988 |
| EP | 472990 | 3/1992 |
| EP | 478319 | 4/1992 |
| EP | 0529775 | 3/1993 |
| EP | 1394270 | 3/2004 |
| EP | 1564306 | 2/2005 |
| JP | 62265567 | 11/1987 |
| JP | 03-236777 | 10/1991 |
| JP | 3236777 | 10/1991 |
| WO | WO 8911101 | 5/1989 |
| WO | WO 9109141 | 6/1991 |
| WO | WO 9119023 | 12/1991 |
| WO | WO 9210092 | 6/1992 |
| WO | WO 9302360 | 2/1993 |
| WO | WO 9306121 | 4/1993 |
| WO | WO 9324517 | 12/1993 |
| WO | WO 9325563 | 12/1993 |
| WO | WO 9400810 | 1/1994 |
| WO | WO 9428028 | 9/1994 |
| WO | WO 9509248 | 4/1995 |
| WO | WO 9512608 | 5/1995 |
| WO | WO 9512808 | 5/1995 |
| WO | WO 9600148 | 1/1996 |
| WO | WO 9602558 | 2/1996 |
| WO | WO 9603212 | 2/1996 |
| WO | WO 9604547 | 2/1996 |
| WO | WO 9607917 | 3/1996 |
| WO | WO 9630392 | 10/1996 |
| WO | WO 9641011 | 12/1996 |
| WO | WO 9714028 | 4/1997 |
| WO | WO 9722720 | 6/1997 |
| WO | WO 9739151 | 10/1997 |
| WO | WO 9740383 | 10/1997 |
| WO | WO 9740385 | 10/1997 |
| WO | WO 9745559 | 12/1997 |
| WO | WO 9802752 | 1/1998 |
| WO | WO 9804950 | 2/1998 |
| WO | WO 9806007 | 2/1998 |
| WO | WO 9820153 | 5/1998 |
| WO | WO 9821593 | 5/1998 |
| WO | WO 9838334 | 9/1998 |
| WO | WO 9840726 | 9/1998 |
| WO | WO 9853093 | 11/1998 |
| WO | WO 9909217 | 2/1999 |
| WO | WO 9918434 | 4/1999 |
| WO | WO 9919515 | 4/1999 |
| WO | WO 9924822 | 5/1999 |
| WO | WO 9935499 | 7/1999 |
| WO | WO 9936564 | 7/1999 |
| WO | WO 9941273 | 8/1999 |
| WO | WO 9951773 | 10/1999 |
| WO | WO 9960170 | 11/1999 |
| WO | WO 9967641 | 12/1999 |
| WO | WO 0003004 | 1/2000 |
| WO | WO 0004372 | 1/2000 |
| WO | WO-00/07019 | 2/2000 |
| WO | WO 0007019 | 2/2000 |
| WO | WO 0013004 | 3/2000 |
| WO | WO 0020593 | 4/2000 |
| WO | WO 0022172 | 4/2000 |
| WO | WO 0026920 | 5/2000 |
| WO | WO 0031356 | 6/2000 |
| WO | WO 0039587 | 7/2000 |
| WO | WO 0046602 | 8/2000 |
| WO | WO 0051058 | 8/2000 |
| WO | WO 0062048 | 10/2000 |
| WO | WO 0073777 | 12/2000 |
| WO | WO 0075373 | 12/2000 |
| WO | WO 0101184 | 1/2001 |
| WO | WO 0120179 | 3/2001 |
| WO | WO 0136679 | 5/2001 |
| WO | WO 0154813 | 8/2001 |
| WO | WO 0156216 | 8/2001 |
| WO | WO 0184150 | 11/2001 |
| WO | WO 0188535 | 11/2001 |
| WO | WO 0194947 | 12/2001 |
| WO | WO 0198765 | 12/2001 |
| WO | WO-02/12888 | 2/2002 |
| WO | WO 0212888 | 2/2002 |
| WO | WO 0214864 | 2/2002 |
| WO | WO 0231182 | 4/2002 |
| WO | WO 0233084 | 4/2002 |
| WO | WO 0235441 | 5/2002 |
| WO | WO 0237209 | 5/2002 |
| WO | WO 02057496 | 7/2002 |
| WO | WO 02058379 | 7/2002 |
| WO | WO 02061121 | 8/2002 |
| WO | WO 02079490 | 10/2002 |
| WO | WO 02084285 | 10/2002 |
| WO | WO-02/096979 | 12/2002 |
| WO | WO 02096979 | 12/2002 |
| WO | WO-03/025011 | 3/2003 |
| WO | WO 03020968 | 3/2003 |
| WO | WO 03025011 | 3/2003 |
| WO | WO 03034029 | 4/2003 |
| WO | WO 03058196 | 7/2003 |
| WO | WO 03079401 | 9/2003 |
| WO | WO 03092546 | 11/2003 |
| WO | WO 2004035426 | 4/2004 |
| WO | WO 2005000236 | 1/2005 |
| WO | WO 2005042763 | 5/2005 |
| WO | WO 2005045059 | 5/2005 |
| WO | WO 2005095650 | 10/2005 |
| WO | WO 2008040257 | 4/2008 |
| WO | WO 2009088893 | 7/2009 |
| WO | WO 2010025002 | 3/2010 |

(56) References Cited

FOREIGN PATENT DOCUMENTS

| WO | WO 2010026038 | 3/2010 |
|---|---|---|
| WO | WO 2010098765 | 9/2010 |
| WO | WO 2010143678 | 12/2010 |

OTHER PUBLICATIONS

Lin et al. "Raman studies of bovine serum albumin", Biopolymers, vol. 15: 203-218 (1976).
MacBeath et al. "Printing proteins as microarrays for high-throughput function determination". Science. vol. 289: 1760-1763 (200).
Morag et al. "Immobilized nitro-avidin and nitro-streptavidin as reusable affinity matrices for application in avidin-biotin technology". Analytical Biochemistry, vol. 243: 257-263 (1996).
Roberts et al. "Patterned magnetic bar array for high-throughput DNA detection" IEEE Transaction on Magnetics. vol. 40, No. 4: 3006-3008 (2004).
Sehgal et al. "A method for the high efficiency of water-soluble carbodiimide-mediated amidation". Analytical Biochemistry. vol. 218: 87-91 (1994).
Takeda et al. "Conformational change of bovine serum albumin by heat treatment", J. Protein Chemistry, vol. 8, No. 5, 653-659 (1989).
Tobitani et al. "Heat-induced gelation of globular proteins. 2. Effect of environmental factors on single-component and mixed-protein gels". Macromolecules. vol. 30: 4855-4862 (1997).
Tobitani et al. "Heat-induced gelation of globular proteins. 1. Model for the effects of time and temperature on the gelation time of BSA gels." Macromolecules. vol. 30:4845-4854 (1997).
Vaynberg et al. "Structure and extent of absorbed gelatin on acrylic latex and polystyrene colloidal particles". Journal of Colloid and Interface Science. vol. 205:131-140 (1998).
Wittemann et al. "Interaction of Proteins with Spherical Polyelectrolyte Brushes" (Polymer Institute, University of Karisruhe, Karlsruhe, Germany) Poster Oct. 2001.
International PCT Search Report PCT/US04/31058 published Mar. 22, 2006.
Armstrong et al., "Suspension arrays for high throughput, multiplexed single nucleotide polymorphism genotyping" Cytometry. vol. 40:102-108 (2000).
Bortolin, S. et al. "Analytical validation of the tag-it high-throughput microsphere-based universal arrray genotyping platform: application to the multiplex detection of a panel of thrombophilia-associated single-nucleotide polymorphisms" Clinical Chemistry, vol. 50 (11), pp. 2028-2036 (Sep. 13, 2004).
B.-Y. Ha et al., "Counterion-Mediated Attraction between Two Like-Charged Rods," Physical Review Letters, Aug. 18, 1997, vol. 79, No. 7, pp. 1289-1292.
A. Hatch, et al., "Diffusion Immunoassay in Polyacrylamide Hydrogels". Micro Total Analysis Systems, pp. 571-572 (2001).
Aho et al., "Efficient String Matching: An Aid to Bibliographic Search". Communications of the ACM, vol. 18, No. 6, pp. 333-340 (Jun. 1975).
Albergo et al., "Solvent effects on the thermodynamics of double-helix formation in (dG-sC) 3". Biochemistry, vol. 20, No. 6: 1413-1418 (1981).
Albrecht et al, "Probing the role of multicellular organization in three-dimensional microenvironments". Nature Methods, vol. 3, No. 5, pp. 369-375 (May 2006).
Albrecht et al., "Photo and electropatterning of hydrogel-encapsulated living cell arrays", Lab on a Chip, vol. 5, Issue 1, pp. 111-118 (2004).
Al-Soud, W. A., "Purification and Characterization of PCR-Inhibitory Components in Blood Cells". Journal of Clinical Microbiology, vol. 39, No. 2, pp. 485-493 (Feb. 2001).
Al-Soud, W. A., et al., "Identification and characterization of immunoglobulin G in blood as a major inhibitor of diagnostic PCR". Journal of Clinical Microbiology, vol. 38, No. 1, pp. 345-350 (Jan. 2000).
Ambruso, D. R., et al., "Experience with donors matched for minor blood group antigens in patients with sickle cell anemia who are receiving chronic transfusion therapy", Transfusion, vol. 27, No. 1, 1987, pp. 94-98.
Zhang, Y., et al., "Reproducible and inexpensive probe preparation for oligonucleotide arrays". Nucleic Acids Research, vol. 29, No. 13, pp. E66-6 (Jul. 1, 2001).
Arenko, et al., "Protein microchips: Use for immunoassay and enzymatic reactions". Analytical Biochemistry, vol. 278, pp. 123-131 (2000).
Assie et al., Correlation between low/high affinity ratios for 5-HT Receptors and Intrinsic Activity, European Journal of Pharmacology, vol. 386, pp. 97-103 (1999).
Bakewell et al., "Characterization of the dielectrophoretic movement of DNA in micro-fabricated structures", Institute of Physics Conference Series (1999) Electrostatics (1999).
Balass et al. "Recovery of high-affinity phage from a Nitrostretavidin matrix in phage-display technology". Analytical Biochemistry. vol. 243: 264-269 (1996).
Baldwin, et al., "Phosphorylation of gastrin-17 by epidermal growth factor-stimulated tyrosine kinase". Nature, vol. 44, pp. 2403-2404 (1998).
Bandeira-Melo, C., et al., "EliCell: A gel-phase dual antibody capture and detection assay to measure cytokine release from eosinophils". Journal of Immunological Methods, vol. 244, pp. 105-115 (2000).
Bao, Y. P., et al., "Detection of Protein Analytes via Nanoparticle-Based Bio Bar Code Technology". Anal. Chem., vol. 78, pp. 2055-2059 (2006).
Barany, Francis, "Genetic Disease Detection and DNA Amplification using Cloned Thermostable Ligase". Proceedings of the National Academy of Sciences of the United States of America, vol. 88, pp. 189-193 (Jan. 1991).
Barnard et al. "A fibre-optic chemical sensor with descrete sensing sites". Nature, vol. 353:338-340 (1991).
Basu, S., et al., "Synthesis and Characterization of a Peptide Nucleic Acid Conjugated to a D-Peptide Analog of Insulin-like Growth Factor 1 for Increased Cellular Uptake". Bioconjugate Chem, vol. 8, No. 4, pp. 481-488 (1997).
Battersby et al., "Toward Larger Chemical Libraries: Encoding with Fluorescent Colloids in Combinatorial Chemistry". J. Amer Chem Soc, vol. 122, pp. 2138-2139 (2000).
Baumgarth N. et al., A practical approach to multicolor flow cytometry for immunophenotyping, J. Immunological Methods, 2000, pp. 77-97, vol. 243.
Bavykin, S.G., et al., "Portable system for microbial sample preparation and oligonucleotide microarray analysis". Appl. Environmental Microbiol. 67(2), 922-928 (2001).
Beatty et al. "Probability of Finding HLA-mismatched Related or Unrelated Marrow or Cord Blood Donors", Human Immunology, 2001, vol. 61, pp. 834-840.
Beebe et al., "Functional Hydrogel structures for autonomous flow control inside microfluidic channels". Nature, vol. 404, No. 6778, pp. 588-590 (Apr. 6, 2000).
Beiboer, S. W., et al., "Rapid genotyping of blood group antigens by multiplex polymerase chain reaction and DNA microarray hybridization" 45 Transfusion 667-679 (2005).
Bennett, P. R., et al., "Prenatal Determination of Fetal RhD Type by DNA Amplification". The New England Journal of Medicine, vol. 329, No. 9, pp. 607-610 (Aug. 26, 1993).
Bernard, Philip S., "Homogenous Multiplex Genotyping of Hemochromatasis Mutations with Fluorescent Hybridization Probes". American Journal of Pthology, vol. 153, No. 4, pp. 1055-1061 (1998).
Bessetti, J., "An introduction to PCT Inhibitors". Profiles in DNA-PCR Inhibition, pp. 9-10 (Mar. 2007).
Bickel, P. J., "Discussion of the Evaluation of Forensic DNA Evidence". Proc. Natl. Acad. Sci., vol. 94, p. 5497 (May 1997).
Zhang, X., et al., "Strand invasion by mixed base PNAs and a PNA-peptide chimera". Nucleic Acids Research, vol. 28, No. 17, pp. 3332-3338 (2000).
Blaaderen, et al., "Synthesis and Characterization of Colloidal Dispersions of Fluorescent, Monodisperse Silica Spheres". Langmuir, vol. 8, No. 2, pp. 2921-2931 (1992).
Bonnet, G., et al., "Thermodynamic basis of the enhanced specificity of structured DNA probes," Proc. Natl. Acad. Science, USA, vol. 96, pp. 6171-6176, May 1999.

(56) References Cited

OTHER PUBLICATIONS

Bos et al., "Controlled release of pharmaceutical protein from hydrogels". Business Briefing: Pharmatech, pp. 184-187 (2002).
Boyce, et al. "Peptidosteroidal Receptors for Opioid Peptides. Sequence-Selective Binding Using a Synthetic Receptor Library". J. Am. Chem. Soc., vol. 116, No. 17, pp. 7955-7956 (1994).
Boyd et al., "Tosyl Chloride activation of a rayon/polyester cloth for protein immobilization", Biotechnology Techniques, Apr. 1993, vol. 7, 4:277-282.
Braga et al., "Hydrophobic Polymer Modification with Ionic Reagents: Polysterene Staining with Water-Soluble Dyes". Langmuir, vol. 19, No. 18, pp. 7580-7586 (2003).
Breslauer, K.J. et al., "Predicting DNA duplex stability from the base sequence". PNAS USA, vol. 83, pp. 3746-3750 (1986).
Brick, et al., "Formation of Colloidal Dispersions of Organic Materials in Aqueous Media by Solvent Shifting". Langmuir, vol. 19, No. 16, pp. 6367-6380 (Jan. 31, 2003).
Broude et al., "Multiplex allele-specific target amplification based on PCR suppression". PNAS. vol. 98, No. 1, pp. 206-211 (2001).
Brown, Patrick O., et al., "Exploring the new world of the genome with DNA microarrays". Nature Genetics Supplement, vol. 21, pp. 33-37 (Jan. 1999).
Buck et al., "Design Strategies and Performance of Custom DNA Sequence Primers". BioTechniques, vol. 27, pp. 528-536 (Sep. 1999).
Bunce et al., "Phototyping: Comprehensive DNA Typing for HLA-A, B, C, DRB1, DRB2, DRB3, DRB4, DRB5 & DQB1 by PCR with 144 primer mixes utilizing sequence-specific primers (PCR-SSP)". Tissue Antigens, vol. 46, No. 5, pp. 355-367 (Nov. 1995).
Bunce, M., et al., "Comprehensive serologically equivalent DNA typing for HLA-A by PCR using sequence specific primers (PCR_SSP)", Tissue Anitigens 45 : 81-90 (1995).
Burbulis, I, et al., "Using protein-DNA chimeras to detect and count small numbers of molecules". Nature Methods, vol. 2, No. 1, pp. 31-37 (Jan. 2005).
Cai et al., "Flow cytometry-based minisequencing: A new platform for high-throughput single-nucleotide polymorphism scoring", Genomics 66:135-143 (2000).
Campbell, C. J., et al., "Cell Interaction Microarray for Blood Phenotyping". Analytical Chemistry, vol. 78, pp. 1930-1938 (2006).
Campian et al. Colored and fluorescent solid supports. Innovation and Perspectives in Solid Phase Synthesis. Ed: E. Birmingham (Mayflower, London), pp. 469-474 (1994).
Cao et al., "High and intermediate resolution DNA typing systems for class I HLA-A, B, C genes by hybridization with sequence-specific oligonnucleotide probes (SSOP)", Rev Immunogenetics 1:177-208 (1999).
Cao et al., "Nanoparticles with Raman Spectroscopic Fingerprints for DNA and RNA Detection" , Science 197:1536-1539 (2002).
Caruso et al., "Magnetic Core-Shell Particles: Preparation of Magnetite Multilayers on Polymer Latex Microspheres". Advanced materials, vol. 11, No. 11, pp. 950-953 (1999).
Caruso, et al., "Magnetic Nanocomposite Particles and Hollow Spheres Constructed by a Sequential Layering Approach". Chem Mater, vol. 13, No. 1, pp. 109-116 (2001).
Caruso. "Nanoengineering of Particle Surfaces". Advanced Materials, vol. 12, No. 1, pp. 11-22 (2001).
Casnellie JE, et al., "Phosphorylation of synthetic peptides by a tyrosine protein kinase from the particulate fraction of a lymphoma cell line". Proc natl Sci USA, vol. 79, No. 2, pp. 282-286 (1982).
Chalmers, et al., "An instrument to determine the magnetophoretic mobility of labeled, biological cells and paramagnetic particles". Journal of Magnetism and Magnetic Materials, vol. 194, pp. 231-241 (1999).
Chan et al. The Bipohysics of DNA Hybridization with Immobilized Oligonucleotide Probes. Biophysical Journal 69: pp. 2243-2255 (1995).
Chang, et al., "New Approach to Produce monosized Polymer Microcapsules by the Solute Co-diffusion Method". Langmuir, vol. 17, No. 18, pp. 5435-5439 (2001).

Zhang et al., "Reconstruction of DNA sequencing by hybridization". Bioinformatics, vol. 19, No. 1, pp. 14-21 (2003).
Chaudhry et al., "Reactivity of human apurinic/apyrimidinic endonucleoase and *Escheria coli* exonucleonase III with bistranded abasic sites in DNA". The Journal of Biological Chemisty., vol. 272: 15650-15655 (1997).
Chee, M. et al., "Accessing genetic information with high-density DNA arrays". Science, vol. 274, pp. 610-613 (1996).
Chen et al., "A Microsphere-Based assay for multiplexed single nucleotide polymorphism analysis using single base chain extension", Genome Research, Cold Spring Harbor Laboratory Press 10:549-557 (2000).
Zhang et al., "Nuclear DNA analysis in genetic studies of populations; practice, problems and prospects" Molecular Ecology. vol. 12:563-584 (2003).
Chen, YX, et al., "Deletion of arginine codon 229 in the Rhce gene alters e and f but not c antigen expression". vol. 44, No. 3, pp. 391-398 (Mar. 2004).
Cheng, et al., "A Synthetic peptide derived from p34cdc2 is a Specific and Efficient Substrate of SRC-Family Tyrosine Kinases". J Biol Chem, pp. 9248-9256. vol. 267, No. 13 (1992).
Zborowski, et al., "Continuous cell separation using novel magnetic quadruple flow sorter". Journal of Magnetism and Magnetic Materials, vol. 194, pp. 224-230 (1999).
Cherepinsky, Vera, "On mathematical aspects of genomic analysis", Ph.D. Thesis, published Mar. 2004.
Cheung, V. G., et al., "Making and Reading Microarrays". vol. 21, pp. 15-19 (Jan. 1999).
Choi, et al., "An on-chip magnetic separator using spiral electromagnets with semi-encapsulated permalloy". Biosensors & Bioelectronics, vol. 16, pp. 409-416 (2001).
Yellen, B. B., et al., "Programmable Assembly of Colloidal Particles Using Magnetic Microwell Templates". Langmuir, p. est 6.5 (2004).
Clerc, P., et al., "Advanced deep reactive ion etching: a versatile tool for microelectromechanical systems". J. Micromech Microeng, vol. 8, No. 4, pp. 272-278 (Dec. 1998).
Coffer et al., "Characterization of Quanum-Confined CdS Nanocrystallites Stabilized by Deoxyribonucleic Acid (DNA)" Nanotechnology, 1992 3:69-75.
Yeh, S. R., et al., "Assembly of ordered colloidal aggregares by electric-field-induced fluid flow". Nature, Mar. 6, 1997; vol. 386, No. 6620, pp. 57-59.
Colombie, et al., "Role of Mixed Anionic-Nonionic Systems of Surfactants in the Emulsion Polymerization of Styrene: Effect on Particle Nucleation". Macromolocules, vol. 33, No. 20, pp. 7283-7291 (2000).
Cosgrove et al. "A Small-angle neutron scattering study of the structure of gelatin at the surface of polystyrene latex particles". Langmuir. vol. 14:5376-5382 (1998).
Coyne et al., "Assymetric PCR for ssDNA Production", Molecular Biology Techniques Manual. Third Edition. Jan. 1994, Feb. 2001; http://www.mcb.uct.ac.za/pcrcond.htm.
Crisp, M., et al., "Preparation of Nanoparticle Coatings on Surfaces of Complex Geometry". Nano Letters, vol. 3, No. 2, pp. 173-177 (2003).
Cronin M.T. et al., "Cystic Fibrosis Mutation Detection by Hybridization to Light-Generated DNA Probe Arrays," Human Mutation, John Wiley & Sons, Inc., US, vol. 7, No. 3, pp. 244-255 (Jan. 1996).
Cruse et al., "Illustrated Dictionary of Immunology". Boca Raton: CRC Press, p. 512 (2003).
Dai-Wu Seol, et al., "Signaling Events Triggered by Tumor Necrosis Factor-related Apoptosis-inducing Ligand (TRAIL): Caspase-8 is Required for TRAIL-Induced Apoptosis". Cancer Research, vol. 61, pp. 1138-1143 (2001).
Dasgupta, et al., "Flow of multiple fluids in a small dimension". Analytical Chemistry, vol. 74, No. 7, pp. 208-213 (2002).
De Farias, P., et al., Investigation of red blood cell antigens with highly fluorescent and stable semiconductor quantum dots, J. Bimedical Optics, 2005, pp. 1-4, vol. 10(4).
Decher, G., "Fuzzy Nanoassemblies: Toward Layered Polymeric Multicomposites". Science, vol. 277, pp. 1232-1237 (Aug. 29, 1997).

(56) References Cited

OTHER PUBLICATIONS

Denomme, G. A., et al., "High throughput multiplex single-nucloetide polymorphism analysis for red cell and platelet antigen genotypes". Transfusion, vol. 45, pp. 660-666 (May 2005).
Denkov et al. "Mechanism of Formation of Two-Dimensional Crystals from Latex Particles on Substrates," langmuir, 1992, pp. 3183-3190, vol. 8.
Ding et al., "Direct molecular haplotyping of long-range genomic DNA with M1-PCR", Jun. 2003, vol. 100, 13: 7449-7453.
Du et al., "Sensitivity and Specificity of Metal Surface-Immobilized," Molecular Beacon, Biosensors; JACS 2005, vol. 127, No. 21, pp. 7932-7940.
Duggan, David J., et al., "Expression profiling using cDNA microarrays". Nature Genetics Supplement, vol. 21, pp. 10-14 (Jan. 1999).
Dunbar SA et al. "Application of the luminex LabMAP in rapid screening for mutations in the cystic fibrosis transmembrane conductance regulator gene: A pilot study" Clin Chem Sep. 2000; 46(9): 1498-500. with Abstract data, pp. 1 and 2.
Duquesnoy HLA Matchmaker: A Molecularly Based Algorithm for Histocompatibility Determination. I. Description of the Algorithm. Human Immunology, vol. 63, pp. 339-352 (2002).
Dziennik, S. R., et al., "Nondiffusive mechanisms enhance protein uptake rates in ion exchange particles". PNAS, vol. 100, No. 2, pp. 420-425 (2003).
Easteal, S. "DNA Fingerprinting by PCR Amplification of HLA Genes". DNA and Criminal Justice; Human Genetics Group, John Curtin School of Medical Research, pp. 121-127 (1991).
Egner et al. "Tagging in combinatorial chemistry: the use of coloured and fluorescent beads". Chem. Commun. pp. 735-736 (1997).
Elaissari et al., "Hydrophilic and cationic latex particles for the specific extraction of nucleic acids". J. Biomater, Sci Polymer Edn, vol. 10, pp. 403-420 (1999).
Erdogan et al., "Detection of mitochondrial single nucleotide polymorphisms using a primer elongation reaction on oligonucleotide microarrays", Nucleic Acid Research, 29 : 1-7 (2001).
Ericsson, O., et al., "A dual-tag microarray platform for high-performance nucleic acid and protein analyses". Nucleic Acids Research, vol. 36, No. 8 e45, pp. 1-9 (2008).
Erlich, et al., "HLA DNA Typing and Transplantation", Immunity, 14: 347-356 (2001).
Fan et al., "Parallel Genotyping of Human SNPs Using Generic High-density Oligonucleotide Tag Arrays", Genome Research, vol. 10, pp. 853-860 (2000).
Fatin-Rouge, N., et al., "Diffusion and Partitioning of Solutes in Agarose Hydrogels: The Relative Influence of Electrostatic and Specific Interactions", J. Phys. Chem. B., vol. 107, pp. 12126-12137 (2003).
Ferguson et al., "High-Density Fiber-Optic DNA Random Microsphere Array". Anal. Chem, vol. 72, pp. 5618-5624 (2000).
Filipovich et al., "Impact of donor type on outcome of bone marrow transplantation for Wiskott-Aldrich syndrome: collaborative study of the International Bone Marrow Transplant Registry and the National Marrow Donor Program", Blood, vol. 97, No. 6, pp. 1598-1603 (2001).
Finkel, et al. "Barcoding the Microworld". Analytical Chemistry, pp. 353-359 (Oct. 1, 2004).
Fitch, J.P. et al., "Rapid Development of Nucleic Acid Diagnostics", Proceedings of the IEEE 90 (11): 1708-1720 (Nov. 2002).
Fluorescent Microspheres (Tech. Note #19). Bangs Laboratories (1997).
Fodor, S., et al., "Light-Directed, Spatially Addressable Parallel Chemical Synthesis". Research Article (Authors are at the Affymax Research Institute, 3180 Porter Drive, Palo Alto, CA 94304), pp. 767-773 (Feb. 15, 1991).
Fowke, Keith R., et al. "Genetic analysis of human DNA recovered from minute amounts of serum or plasma". Journal of Immunological Methods, vol. 80, pp. 45-51 (1995).

Frengen, Jomar, et al., "Demonstration and Minimization of Serum Interference in Flow Cytometric Two-Site Immunoassays". Clinical Chemistry, vol. 40, No. 3, pp. 420-425 (1994).
Fuh et al. Single Fibre Optic Fluorescence pH Probe. Analyst, 112:1159-1163 (1987).
Fuh et al., "A Method for Determination of Particle Magnetic Susceptibility with Analytical Magnetapheresis". Anal. Chem, vol. 72, pp. 3590-3595 (2000).
Fulton et al. "Advanced multiplexed analysis with the FlowMetrix system". Clinical Chemistry, vol. 43:9, pp. 1749-1756 (1997).
Gahan, P. B., "Circulating Nucleic Acid in Plasma and Serum: Diagnosis and Prognosis in Cancer". Oncology, vol. 32, No. 6, pp. 20-22 (Oct. 2008); Weekly news updates on www.cli-online.com.
Garber, K. "More SNPs on the Way". Science, vol. 281, No. 5384, pp. 1788-1790 (Sep. 18, 1998).
Gates, et al., "Photonic Crystals that can be Addressed with an External Magnetic Field". Adv Mater, vol. 13, No. 21, pp. 1605-1608 (2001).
Gelfi, C., et al., "Investigation of the Properties of Novel Acrylamido Monomers by Capilary Zone Electrophoresis", Journal of Chromatography, vol. 608, pp. 333-341 (1992).
Gerlach. Human Lymphocyte Antigen Molecular Typing. Archives of Pathology & Laboratory Medicine. vol. 126, pp. 281-284 (2002).
Ghazaly, et al., "Synthesis and Characterization of a Macromonomer Crosslinker". Journal of Applied Polymer Science, vol. 77, pp. 1362-1368 (2000).
Ghosh et al. "Covalent attachement of oligonucleotides to solid supports". Nucleic Acids Research. vol. 16, No. 13; pp. 5363-5371 (1987).
Ghosh, P., et al., "A Simple Lithographic Approach for Preparing Patterned, Micron-Scale Corrals for Controlling Cell Growth". Angew. Chem. Int. Ed., vol. 38, No. 11, pp. 1592-1595 (1999).
Giersig et al. Formation of ordered two-dimensional gold colloid lattices by electrophoretic deposition. J. Phys. Chem., vol. 97: 6334-6336 (Apr. 29, 1993).
Giorgi, R., et al., "Nanotechnologies for Conservation of Cultural Heritage: Paper and Canvas Deacidification". Langmuir, vol. 18, pp. 8198-8203 (2002).
Good, L., et al., "Bactericidal antisense effects of peptide-DNA conjugates". Nature Biotechnology, vol. 19, pp. 360-364 (2001).
Goodey et al., "Development of multianalyte sensor arrays composed of chemically derivatized polymeric microspheres localized in micromachined cavitites". Journal of American Chemical Society, vol. 123, pp. 2559-2570 (2001).
Graf et al., "A general method to coat colloidal particles with silica". Langmuir, vol. 19, pp. 6693-6700 (2003).
Grazia et al. In-vivo biomedical monitoring by fiber-optic system. Journal of Lightwave Technology. 13, 1396-1406 (1995).
Yellen, et al., "Statistical Analysis of Weakest Link in Chains of Magnetic Particle Carriers for Applications in Printing Biochemical Arrays". European Cells and Materials, vol. 3, pp. 88-91 (2002).
Grondahl, et al., "Encoding Combinatorial Libraries: A Novel Application of Fluorescent Silica Colloids". Langmuir, vol. 16, No. 25, pp. 9709-9715 (2000).
Gruttner, et al., "New types of silica-fortified magnetic nanoparticles as tools for molecular biology applications". Journal of Magnetism and Magnetic Materials, vol. 94, pp. 8-15 (1999).
Gubin et al., "Identification of the Dombrock blood group glycoprotein as a polymorphic member of the ADP-ribosyltransferase gene family", Blood, Oct. 1, 2000, vol. 96, No. 7, pp. 2621-2627.
Gullberg, M., et al., "Cytokine detection by antibody-based proximity ligation". PNAS, vol. 101, No. 22, pp. 8420-8424 (Jun. 2004).
Guo, Zhen et al. "Oligonucleotide arrays for high-throughput SNPs detection in the MHC class I genes: HLA-B as a model system". Genome Research; vol. 12, No. 3, pp. 447-457 (Mar. 2002).
Guo, Zhen, "Direct fluorescence analysis of genetic polymorphisms . . . oligonucleotide arrays on glass supports". Nucleic Acids Research, Jul. 1994, Oxford Univ Press, pp. 5456-5465.
Gupta et al. ("Hydrogels: from controlled release to pH-responsive drug delivery" Drug Discov Today. May 15, 2002;7(10):569-79.

(56) References Cited

OTHER PUBLICATIONS

Gustafsdottir, S. M., "In vitro analysis of DNA—protein interactions by proximity ligation". PNAS, vol. 104, No. 9, pp. 3067-3072 (Feb. 2007).

Haab et al. Single Molecule Fluorescence Burst Detection of DNA Fragments Separated by Capillary Electrophoresis. Analytical Chemistry, vol. 67 (No. 18) : 3253-3256 (1995).

Hacis et al., "Resequencing and mutational analysis using oligonucleotide microarrays", Nature America; 21 : 42-47 (1999).

Hakala, H., et al. "Simultaneous detection of several oligonucleotides by time-resolved fluorometry: the use of a mixture of categorized microparticles in a sandwich type mixed-phase hybridization assay". Nucleic Acids Research, vol. 26, pp. 5581-5585 (1998).

Hashimi et al., "A Flexible Array format for large-scale, rapid blood group DNA typing". Transfusion, Published Online Apr. 6, 2004, vol. 45, Issue 5, pp. 680-688 (May 2005).

Hashmi, G., et al, "Determination of 24 minor red blood cell antigens for more than 2000 blood donors by high-throughput DNA analysis". Transfusion, vol. 47, No. 4, pp. 736-747 (Apr. 2007).

Zaer, Farid, et al., "Antibody Screening by Enzyme-Linked Immunosorbent Assay Using Pooled Soluble HLA in Renal Transplant Candidates". Transplantation, vol. 63, No. 1, pp. 48-51 (Jan. 15, 1997).

Heinrich, et al., "Interleukin-6-type Cytokine Signaling through the gp 130/Jak/STAT pathway". Biochem J, vol. 334, pp. 297-314 (1998).

Helgesen, et al., "Aggregation of magnetic microspheres: experiements and simulations". Physical Review Letters, vol. 61, No. 15, pp. 1736-1739 (1998).

Helmuth, R., et al., "HLA-DQ Allele and Genotype Frequencies in Various Human Populations, Determined by Using Enzymatic Amplification and Oligonucleotide Probes". Am. J. Hum. Genet, vol. 47, pp. 515-523 (1990).

Hermanson, G. T., "Nucleic Acid and Oligonucleotide Modification and Conjugation". Bioconjugate Techniques, Academic Press, Chapter 17, pp. 639-671 (Jan. 15, 1996).

Yershov et al., "DNA analysis and diagnostics on oligonulceotide microchips". Proceedings of the National Academy of Sciences of the United States of America, vol. 93, No. 10, pp. 4913-4918 (May 14, 1996).

Hiller, J., et al., "Reversibly erasable nanoporous anti-reflection coatings from polyelectrolyte multilayers". Nature Materials, vol. 1, pp. 59-63 (Sep. 2002).

Hirata, H., et al., "Caspases Are Activated in a Branched Protease Cascade and Control Distinct Downstream Processes in Fas-induced Apoptosis". J. Exp. Med., vol. 187, No. 4, pp. 587-600 (1998).

Hizume, et al., "Tandem repeat DNA localizing on the proximal DAPI bands of chromosomes in *Larix*, pinaceae". Genome, vol. 45, pp. 777-783 (2002).

Holtz, J., et al., "Intelligent Polymerized Crystalline Colloidal Array: Novel Sensor Materials", Analytical Chemistry, vol. 70, No. 4, pp. 780-791 (1998).

Houghton. "General method for the rapid solid-phase synthesis of large numbers of peptides: specificity of anitgen-antibody interaction at the level of individual amino acids". Proc. Natl. Avad. Sci. USA. vol. 82:5131-5135 (1985).

Huff et al., "Technical Milestone: Development of the Logical Observation Identifier Names and Codes (LOINC) Vocabulary". JAIMA, vol. 5, pp. 276-292 (1998).

Iannone, Marie A., et al., "Multiplexed Single Nucelotide Polymorphism Genotyping by Oligonucleotide Ligation and Flow Cytometry". Cytometry, vol. 39, Issue 2, pp. 131-140 (Feb. 17, 2000).

Ide et al., "Synthesis and damage specificity of a novel probe for the detection of abasic sites in DNA". Biochemistry. vol. 32: 8276-8283 (1993).

Ito, Y., et al., "Patterned Immobilization of Thermoresponsive Polymer", Langmuir, vol. 13, pp. 2756-2759 (1997).

Iwayama, et al., "Optically Tunable Gelled Photonic Crystal Covering Almost the Entire Visible Light Wavelength Region", Langmuir (2002).

Jackman, R. J., et al., "Using Elastomeric Membranes as Dry Resists and for Dry Lift-Off", Langmuir, vol. 15, pp. 2973-2984 (1999).

Jeon, N. L., et al., "Patterned polymer growth on silicon surfaces using microcontact printing and surface-initiated polymerization", Applied Physics Letters, vol. 75, No. 26, pp. 4201-4203 (1999).

John C. Guatelli et al., "Isothermal, in vitro amplification of nucleic acids by a multienzyme reaction modeled after retroviral replication,"Proc. Nat'l Academy of Science USA, vol. 87: pp. 1874-1878 (1990).

Johnson, K. L., et al., "Surface Energy and the Contact of Elastic Solids". Proceedings of the Royal Society of London, Series A, Mathematical and Physical Sciences, vol. 324, No. 1558, pp. 301-313 (Sep. 8, 1971).

Jones et al., "Constraint, Optimization, and Hierarchy: Reviewing Stereoscopic Correspondence of Complex Features". Computer Vision and Image Understanding, vol. 65, No. 1, pp. 57-78 (1997).

Jones et al., "Dielectrophoretic liquid actuation and nanodroplet formation", Journal of Applied Physics, vol. 89, No. 2, pp. 1441-1448 (Jan. 15, 2001).

Kakabakos et al. "Immobilization of Immunoglobulins onto Surface-treated and Untreated Polystyrene Beads for Radioimmunoassays" Clin. Chem. 36 (1990), 492-496.

Kalinina, O., et al., "A core-shell Approach to Producing 3D Polymer Nanocomposites", Macromolecules, vol. 32, pp. 4122-4129 (1999).

Kamholz, et al., "Optical measurement of transverse molecular diffusion in a microchannel". Biophysical Journal, vol. 80, pp. 1967-1972 (2001).

Kamm, R. C., et al. "Nucleic Acid Concentrations in Normal Human Plasma". Clinical Chemistry, vol. 18, pp. 519-522 (1972).

Kandimalla et al., "Cyclicons" as Hybridization-Based Fluorescent Primer-Probes: Bloorganic & Medicinal Chemistry 8 (2000) 1911 to 1916.

Kelly, J.J., et al., "Radical-generating coordination complexes as tools for rapid and effective fragmentation and fluorescent labeling of nucleic acids for microchip hybridization". Analytical Biochemisty, vol. 311, No. 2, pp. 103-118 (Dec. 15, 2002).

Klintschar, et al., "Genetic variation at the STR loci D12S391 and CSF1PO in four populations from Austria, Italy, Egypt and Yemen". Forensic Sci. Int. vol. 97:37-45 (1998).

Kim E., et al., "Polymer microstructures formed by moulding in capillaries", Nature, vol. 376, pp. 581-584 (1995).

Knipper, et al., Accession No. AF221125.1.1 on Electronic Database at NCBI (Feb. 16, 2000).

Koch et al., "PNA-Peptide Chimerae". Tetrahedron Letters, vol. 36, pp. 6933-6936 (1995).

Koh, et al., "Molding of Hydrogel Microstructures to Create Multiphenotype Cell Microarrays". Analytical Chemistry (2003).

Koh, et al., "Poly(ethylene glycol) Hydrogel Microstructures Encapsulating Living Cells". Langmuir, vol. 18, pp. 2459-2462 (2002).

Kolch. "Meaningful Relationships: The Regulation of the Ras/Raf/MEK/ERK pathway by protein interactions". Biochem J, vol. 351, pp. 289-305 (2000).

Kotov, N., et al., "Layer-by-Layer Self-Assembly of Polyelectrolyte-Semiconductor Nanoparticle Composite Films". J. Phy Chem, vol. 99, pp. 13065-13069 (1995).

Krausa et al. "A Comprehensive PCR-ssP typing system for identification of HLA-A locus alleles", Tissue Antigens, 47 (3) : 237-244 (1996).

Krsko, P., et al., "Electron-Beam Surface Patterned Poly(ethylene glycol) Microhydrogels". Langmuir, vol. 19, pp. 5618-5625 (2003).

Krutzik P.O. et al., "Fluorescent cell barcoding in flow cytometry allows high-throughput drug screening and signal profiling". Nature Methods, vol. 3, No. 5, pp. 361-368 (2006).

Kubo et al., "A Novel Sensitive and specific assay for abasic sites, the most commonly produced DNA lesion". Biochemistry, vol. 13:3703-3708 (1992).

Kumacheva, E., et al., "Three-dimensional Arrays in Polymer Nanocompositites", Advanced Materials, vol. 11, No. 3, pp. 231-234 (1999).

Kurita-Ochiai, T., et al., "Butyric Acid-Induced T-Cell Apoptosis is Mediated by Caspase-8 and -9 Activation in a Fas-Independent Manner". Clinical and Diagnostic Laboratory Immunology, vol. 8, No. 2, pp. 325-332 (2001).

(56) References Cited

OTHER PUBLICATIONS

Vorlop, K. D., et al., "Entrapment of Microbial Cells within Polyurethane Hydrogel Beads with the Advantage of Low Toxicity", Biotechnology Techniques, vol. 6, No. 6, pp. 483-488 (1992).

Kwoh et al., "Transcription based amplification system and detection of amplified human immunodeficiency virus type 1 with a bead-based sandwich hybridization format". Proc. Natl. Acad. Sci, vol. 86, pp. 1173-1177 (Feb. 1989).

LaForge, K. S., et al., "Detection of Single Nucleotide Polymorphisms of the Human Mu Opioid Receptor Gene by Hybridization of Single Nucleotide Extension on Custom Oligonucleotide Gelpad Microchips: Potential in Studies of Addiction". American Journal of Medical Genetics (Neuropsychiatric Genetics), vol. 96, pp. 604-615 (2000).

Lagerholm et al., "Theory for Ligand Rebinding at Cell Membrane Surfaces," Biophysical Journal (1998), vol. 74, pp. 1215-1228.

Lamb, D. J., et al., "Modification of Natural and Artificial Polymer Colloids by Topology-Controlled Emulsion Polymerization". Biomacromolecules, vol. 2, No. 2, pp. 518-525 (2001).

Lander, E. S. "The New Genomics: Global Views of Biology". Sciences, vol. 274, No. 5287, pp. 536-539 (Oct. 25, 1996).

Lander, E. S., et al., "Array of Hope". Nature Genetics Supplement, Perspective, vol. 21, pp. 3-4, (Jan. 1999).

Latour, P., et al., "Polymorphic Short Tandem Repeats for Diagnosis of the Charot-Marie-Tooth IA Duplication". Clinical Chemistry, vol. 47, pp. 829-837 (2001).

Lau, F. Y., et al., "Provision of phenotype-matched blood units: no need for pre-transfusion antibody screening", Haematologica, vol. 86, No. 7, Jul. 2001, pp. 742-748.

Lee et al. "Quantitation of residual WBCs in filtered blood components by high-throughput, real time kinetic PCR", Blood Components, transfusion, vol. 42, pp. 87-93 (Jan. 2002).

Lee, et al., "Combination of Insulin-like Growth FActor (IGF)-1 and IGF-Binding Protein-1 Promotes Fibroblast-Embedded Collagen Gel Contraction". Endocrinology, vol. 137, pp. 5278-5283 (1996).

Lee, H. J., et al., "Fabricating RNA Microarrays with RNA-DNA Surface Ligation Chemistry". Analytical Chemistry, vol. 77, No. 23, pp. 7832-7837 (Dec. 1, 2005).

Lee, S., et al., "Control of Core-Shell Latex Morphology". Polymer Latexes, ACS Symposium, American Chemical Society, pp. 234-253 (1992).

Lemieux: "high throughput single nucleotide polymorphism genotyping technology" Current Genomics. vol. 1:301-311 (2000).

Lhomme et al. "Abasic DNA structure, reactivity and recognition". Biopolymers. vol. 52 : 65-83 (1999).

Li, A., et al., "Multiplexed analysis of polymorphisms in the HLA gene complex using bead array chips". Tissue Anitigens, vol. 63, pp. 518-528 (2004).

Liang L., et al., "Preparation of Composite-Crosslinked Poly(N-isopropylacrylamide) Gel Layer and Characteristics of Reverse Hydrophilic-Hydrophobic Surface", Journal of Applied Polymer Science, vol. 72, pp. 1-11 (1999).

Liang, L., et al., "Temperature-sensitive membranes prepared by UV photopolymerization of N-isopropyrlacrylamide on a surface of porous hydrophilic polypropylene membranes", Journal of Membrane Science, vol. 162, pp. 235-246 (1999).

Liebert, M. R., et al., "Dynamics of the holes in human erythrocyte membrane ghosts". J. Biological Chemistry, vol. 257, No. 19, pp. 11660-11666 (1982).

Lin et al. "Raman Studies of Bovine Serum Albumin" . Biopolymers 15:203-218 (1976).

Lindahl et al., "Rate of depuriniation of native deoxyribonucleic acid". Biochemistry. vol. 11, No. 19: 3610-1617 (1972).

Lindahl et al., "Rate of chain breakage at apurinic sites in double-stranded deoxyriboncclueic acid" Biochemistry, vol. 11, No. 19:3618-3623 (1972).

Lipshutz, R. J., et al., "High Density Synthetic Oligonucleotide Arrays". vol. 21, pp. 20-24 (Jan. 1999).

Liu, et al., "Development of a Carbon Dioxide-Base Microencapsulation Technique for Aqueous and Ethanol-Based Latexes". Langmuir (2002).

Liu, V, et al, "Three-Dimensional Photopatterning of Hydrogels Containing Living Cell". Biomedical Microdevices, vol. 4, No. 4, pp. 257-266 (2002).

Lofas, et al., "Methods for site controlled coupling to carboxymethyldextran surfaces in surface plasmon resonance sensors". Biosensors & Bioelectronics, vol. 10, pp. 813-822 (1995).

Loomans, E., et al., "Assessment of the functional affinity constant of monoclonal antibodies using an improved enzyme-linked immunosorbent assay". Journal of Immunological Methods, vol. 184, pp. 207-217 (1995).

Ye et al., "Fluorescent Microsphere-Based Readout Technology for Multiplexed Human Single Nucleotide Polymorphism Analysis and Bacterial Identification" Human Mutation, Apr. 17, 2001 (4); 305-16).

Lund et al. Assessment of Methods for Covalent Bonding of Nucleic Acids to Magnetic Beads, Bynabeads, and the Characteristics of the Bound Nucleic Acids in Hybridization Reactions, Nucleic Acids REsearch vol. 16, No. 22, 10861-10880 (1988).

Luo et al., "Emulsion Copolymerization of Butyl Acrylate with Cationic Monomer Using Interfacial Redox Initiator System". Journal of Polymer Science, vol. 39, pp. 2696-2709 (2001).

Lvov, Y, et al., "Alernate Assembly of Ordered Multilayers of SiO2 and Other Nanoparticles and Polyions". Langmuir, vol. 13, pp. 6195-6203 (1997).

MacBeath et al., "Printing proteins as microarrays for high-throughput function determination". Science, vol. 289; pp. 1760-1763 (Sep. 8, 2000).

Maldonado-Rodriguez et al., "Hybridization of glass-tethered oligonucleotide probes to . . . ", Molecular Biotechnology, vol. 11, No. 1, pp. 1-12 (1999).

Marras et al., Multiplex detection of single-nucleotide variations using molecular beacons: Genetic Analysis: Biomolecular Engineering 14 (1999) 151-156.

Marsh, S. G. E., et al., The HLA Facts Book, "HLA Typing at the DNA Level", Academic Press, Chapter 6, pp. 37-39 (2000).

Martin, M., et al. "A Method for Using Serum or Plasma as a Source of DNA for HLA Typing". Human Immunology, vol. 33, pp. 108-113 (1992).

Martinell, J. et al., "Three mouse models of human thalassemia", Proc. Natl. Acad. Sci, USA. Aug. 1981, vol. 78, No. 8, pp. 5056-5060 (see especially p. 5057, col. 1, last paragraph, Figure 4, and the legend to Figure 4.

Maskos, U. et al., "Parallel analysis of oligodeoxyribonucleotide (oligonucleotide) interactions. I. Analysis of factors influencing oligonucleotide duplex formation". Nucleic Acids Research, vol. 20, No. 7, pp. 1675-1678 (1992).

Maskos, U., et al., "Oligonucleotide hybridisations on glass supports: a novel linker for oligonucleoptide synthesis and hybridisation properties of oligonucleotides synthesized in situ". Nucleic Acids Research, vol. 20, No. 7, pp. 1679-1684 (1992).

Matthews et al., "Biochemistry: A Short Course". New York: John Wiley & Sons, Inc, p. 25 (1997).

Maxam et al., "A new method for sequencing DNA," Proc. Natl. Acad. Sci. USA. vol. 74, No. 2, pp. 560-564, Feb. 1977.

McCloskey, et al., "Magnetic Cell Separation: Characterization of Magnetophoretic Mobility". Anal. Chem., vol. 75, pp. 6868-6874 (2003).

McCloskey, et al., "Magnetophoretic Mobilities Correlate to Antibody Binidng Capacities". Cytometry, vol. 40, pp. 307-315 (2000).

Mei et al. "Genome-wide Detection of Allelic Imbalance Using Human SNPs and High-Density DNA Arrays". Genome Research. vol. 10, pp. 1126-1137 (2000).

Michael, et al., "Randomly ordered addressable high-density optical ssensor arrays". Anal. Chem, vol. 70, pp. 1242-1248 (1999).

Micheletto et al., "A simple method for the production of a two-dimensional ordered array of small latex particles". Langmuir, vol. 11, pp. 3333-3336 (1995).

Moller, E., et al., "The Use of Magnetic Beads Coated with Soluble HLA Class I or Class II Proteins in Antibody Screening and for

(56) References Cited

OTHER PUBLICATIONS

Specificity Determination of Donor-Reactive Antibodies". Transplantation, vol. 61, No. 10, pp. 1539-1545 (May 27, 1996).
Moore, et al., "The use of magnetite-doped polymeric microspheres in calibrating cell tracking velocimetry". J. Biochem. Biophys. Methods, vol. 44, pp. 115-130 (2000).
Morag et al. "Immobilized nitro-avidin and nitro-streptavidin as reusable affinity matrices for application in avidin-biotin technology". Analytical Biochemistry. vol. 243: 257-263 (1996).
Mori, et al., Computer program to predict liklihood of finding an HLA-matched donor: Methodology, validation, and application. Biology of Blood and Marrow Transplantation, vol. 2, pp. 134-144 (1996).
Morishima et al., "Microflow system and transportation of DNA molecule by dielectrophoretic force utilizing the conformational transition in the higher order structure of DNA molecule". Proceedings—IEEE Annual International Workshop on Micro Electro Mechanical Systems: An investigation of micro structures, sensors, actuators, machines and robots. Nagoya, Jan. 26-30, 1997.
Muller et al., "Gene and Haplotype Frequencies for the Loci HLA-A, HLB-B, and HLA-DR Based on Over 13,000 German Blood Donors". Human Immunology, 2003, 64: 137-151.
Mullis et al. Specific Synthesis of DNA in Vitro via a Polymerase-Catalyzed Chain Reaction Methods in Enzymology, 1987; vol. 155, pp. 335-350.
Nagarajan et al., "Identifying Spots in Microarray Images", IEEE Transactions on Nanobioscience, vol. 1, No. 2, pp. 78-84 (Jun. 2002).
Nagayama et al., "Fabrication of two-dimensional colloidal arrays". Phase Transitions, vol. 45, 185-203 (1993).
Nam, J., et a., "Colorimetric Bio-Barcode Amplification Assay for Cytokines". Anal. Chem., vol. 77, pp. 6985-6988 (2005).
Nau et al., "A Command Processor for the Determination of Specificities fro Matrices of Reactions Between Blood Cells and Antisera". Computers and Biomedical Research, vol. 10, pp. 259-269 (1977).
Nazarenko et al. (2002) Multiplexed quantifiative PCR using self-quenched primers labeled with a single fluorophore. Nucleic Acids Research, 30 (9), e37.
Niemeyer et al., "DNA-directed Immobilization: Efficient, Reversible, and Site-Selective Surface Binding of Proteins by means of Covalent Stretavidin Conjugates". Analytical Biochemistry, vol. 268, pp. 54-63 (1999).
Niemeyer et al., "Oligonucleotide-directed self-assembly of proteins: semisynthetic DNA—streptavidin hybrid molecules as connectors for the generation of macroscopic arrays and the construction of supramolecular bioconjugates". Nucleic Acids Research, vol. 22, pp. 5530-5539 (1994).
Nygren, "Molecular Diagnostics of Infectious Diseases" Royal Institute of Technology Department of Biotechnology, Stockholm 2000, pp. 1-68.
Ohlmeyer, M. H. J. et al. "Complex Synthetic Chemical Libraries Indexed with Molecular Tags". Proceedings of the National Academy of Sciences, USA, National Academy of Science, Washington DC. vol. 90, Dec. 1, 1993, pp. 10922-10926.
Okubo, and Yamashita. "Thermodynamics for the preparation of micorn-sized, monodispersed highly monomer-'absorbed' polymer particles utilizing the dynamic swelling method." Colloids and Surfaces, 1999:153-159.
Okubo et al., "Preparation of micron-size monodisperse polymer particles by seeded polymerization utilizing the dynamic monomer swelling method". Colloid and Polymer Science, vol. 269, No. 3, pp. 222-226 (1991).
Olejnik et al., "Photocleavable biotin phosphoramidite for 5'-end-labeling, purification & phosphorylation of oligonucleotides", Nucleic Acids Research 1996, vol. 24, 2:361-366.
Oliver, D., et al, "Use of Single Nucleotide Polymorphisms (SNP) and Real-Time Polymerase Chain Reaction for Bone Marrow Engraftment Analysis". Journal of Molecular Diagnostics, vol. 2, No. 4, pp. 202-208 (Nov. 2000).
Olson et al. "A common langauage for physical mapping of the human genome". Science, vol. 245, pp. 1434-1435 (1989).

Otero, T. F., et al., "Electrochemically initiated acrylic acid/acrylamide copolymerization", J. Electroanal. Chem., vol. 256, pp. 433-439 (1998).
Otero, T. F., et al., "Electroinitiated polymerization of acrylamide in DMG: Attempts at an interfacial model", J. Electroanal. Chem., vol. 304, pp. 153-170 (1991).
Pastinen, et al., "A System for specific, high-throughput genotyping by allele-specific primer extension on microarrays". Genome Res., vol. 10, pp. 1031-1042 (2000).
Peter, C., et al., "Optical DNA-sensor chip for real-time detection of hybridization events". Fresenius J. Anal. Chem, vol. 371, pp. 120-127 (Jun. 2001); Published online Springer-Verlay 2001.
Wilson, M. R., et al., "A New Microsphere-based Immunofluorescence Assay for Antibodies to Membrane-associated Antigens". Journal of Immunological Methods, vol. 107, pp. 231-237 (1988).
Peterson, et al. "Fiber Optic pH probe for physiological use". Anal. Chem. vol. 52, 864-869 (1980).
Peterson, et al., "Fiber Optic Sensors for Biomedical Applications". Science, vol. 13; pp. 123-127 (1984).
Peytavi et al., "Correlation between microarray DNA hybridization efficiency and the position of short capture probe on the target nucleic acid". Biotechniques, vol. 39, No. 1, pp. 89-96 (2005).
Pooga, M., et al., "Cell-Penetrating constructs regulate galanin receptor levels and modify pain transmission in vivo" Nature Biotechnology, vol. 16, pp. 857-861 (1998).
Pope. "Fiber optic chemical microsensors employing optically active silica microspheres". SPIE, vol. 2388; pp. 245-256 (1995).
Prati D. et al., DNA Enzyme Immunoassay of the PCR-Amplified HLA-DQ Alpha Gene for Estimating Residual Leukocytes in Filtered Blood Clincial and Diagnostic Laboratory Immunology, Mar. 1995, p. 182-185.
Pregibon et al, "Magnetically and Biologically Active Bead-Patterned Hydrogels". Langmuir, vol. 22, pp. 5122-5128 (2006).
Preza, "Phase Estimation using rotational diversity for differential interference contrast microscopy". Dissertation presented to the Washington University, Server Institute of Technology, Department of Electrical Engineering; St. Louis, MO (Aug. 1998).
Proudinikov et al., "Chemical methods of DNA and RNA fluorescent labeling". Nucleic Acids Research. vol. 24, No. 22: 4535-4542 (1996).
Proudnikov, D., et al., "Immobilization of DNA in Polyacrimide Gel for the Manufacture of DNA and DNA-Oligonucleotide Microchips", Analytical Biochemistry, vol. 259, pp. 34-41 (1998).
Quon, R., et al., "Measurement of the Deformation and Adhesion of Rough Solids in Contact". J. Phys. Chem., vol. 103, pp. 5320-5327 (1999).
Rabbany et al., "Assessment of hetrogeneity in antibody displacement reactions". Anal Chem, vol. 69, pp. 175-182 (1997).
Radtchecnko et al., "Core-shell structures formed by the solvent-controlled precipitation of luminescent ScTe nanocrystals on latex spheres". Advanced Materials, vol. 13, No. 22, pp. 1684-1687 (2001).
Radtkey et al., "Rapid, high-fidelity analysis of simple sequence repeats on an electronically active DNA microchip". Nucleic Acids Research, vol. 28, No. 7, p. e17 (2000).
Ramsay, G., "DNA Chips: State-of-the-Art". Nature Biotechnology, vol. 16, pp. 40-44 (Jan. 1998).
Reddy et al., "Determination of the Magnetic Susceptibility of Labeled Particles by Video Imaging". Chemical Engineering Science, vol. 51, No. 6, pp. 947-956 (1996).
Reid M.E., et al., "Novel Dombrock blood group genetic variants . . . ", Blood (ASH Annual Meeting Abstract) 2004, 104: Abstract 383.
Relogio, A. et al., "Optimization of oligonucleotide-based DNA microarrays", Nucl. Acids Res., vol. 30, e51, pp. 1-10 (2002).
Richardson et al., "The use of coated paramagnetic particles as a physical label in a magneto-immunassay". Biosensors & Bioelectronics, vol. 16, pp. 989-993 (2001).
Richardson, et al., "A novel measuring system for the determination of paramagnetic particle lables for use in magneto-immunoassays". Biosensors & Bioelectronics, vol. 16, pp. 1127-1132 (2001).

(56) References Cited

OTHER PUBLICATIONS

Richetti et al., "Two-dimensional aggregations and crystallization of a colloidal suspension of latex spjeres", J. Physique Letter. vol. 45, pp. L-1137 to L-1143 (1984).
Righetti, P. G., et al., "Electrophoresis gel media: the state of the art", J. Chromatogr B., Biomed Sci Appl, vol. 699, No. 1-2, pp. 63-75 (Oct. 10, 1997).
Roberts et al. "Patterned magnetic bar array for high-thoughput DNA detection" IEEE Transaction on Magnetics. vol. 40, No. 4: 3006-3008 (2004).
Rubina et al, "Hydrogel drop microchips with immobilized DNA: properties and methods for large-scale production". Analytical Biochemistry, vol. 325, pp. 92-106 (2004).
Rudzinski, et al., "pH-sensitive acrylic-based copolymeric hydrogels for the controlled release of a pesticide and a micronutrient". Journal of Applied Polymer Science, vol. 87, pp. 394-403 (2003).
Sacchetti, et al. "Efficiency of Two Different Nine-Loci Short Tandem Repeat Systems for DNA Typing Purposes". Clinical Chemistry, vol. 45, No. 2, pp. 178-183 (1999).
Saito, K., et al., "Detection of Human Serum Tumor Necrosis Factor-alpha in Healthy Donors, Using a Highly Sensitive Immuno-PCR Assay". Clinical Chemistry, vol. 45, No. 5, pp. 665-669 (1999).
Sambrook et al., "Precipitation with Ethanol or Isopropanol", Concentrating Nucleic Aicds, Molecular Cloning vol. 3, pp. E3-E4 and E.10-E.15 (1989).
Sano, T, et al., "Immuno-PCR: Very Senisitive Antigen Detection by Means of Specific Antibody-DNA Conjugates". Science, vol. 258, pp. 120-122 (Oct. 2, 1992).
Santa Lucia, J. Jr., "A unified view of polymer, dumbbell, and oligonucleotide DNA nearest-neighbor thermodynamics". PNAS USA, vol. 95, pp. 1460-1465 (1998).
Schaid et al., "Score Tests for Association between traits and Haplotypes when Linkage Phase is Ambiguous", American Journal of Genetics. vol. 70, pp. 425-434 (2002).
Schena et al., "Quantitative Monitoring of Gene Expression Patterns with a Complementary DA Microarray". Science, vol. 270, pp. 467-470 (1995).
Schouten, Jan P., et al., "Relative Quantification of 40 Nucleic Acid Sequences by Multiplex Ligation-Dependent Probe Amplification". Nucleic Acids Research, vol. 30, No. 12, e57 (Jun. 15, 2002).
Schreiber, G. B., et al., "Increasing Blood Availability by changing Donation Patterns". Transfusion, vol. 43, pp. 591-597 (2003).
Schreuder et al., "The HLA Dictionary 1999: A Summary of HLA-A, B, C, DRB1/3/4/5, DOB1 alleles and their association with serologically defined HLA-A, B, C, DR and DQ antigens", Tissue Antigens 54 : 409-437 (1999).
Schumaker, et al. "Mutation Detection by solid phase primer extension", Human Mutation 7:346-354 (1996).
Wilson et al., "A generalized method for magnetite nanoparticle steric stabilization utilizing block copolymers containing carboxylic acids". European Cells and Materials, vol. 2, Suppl 2, pp. 202-209 (2002).
Schuster et al. "Allele-specific and asymetric polymerase chain reacton amplification in combination: a one step polymerase chain protocol for rapid diagnosis of familial defective apolipoprotein B-100", Anal Biochem. Jul. 1992; 204 (1):22-5).
Scillian, James J., et al., "Early Detection of Antibodies Against rDNA-Produced HIV Proteins with a Flow Cytometric Assay". Clinical Chemistry, vol. 40, No. 3, pp. 420-425 (1994).
Scott et al., "Properties of Fluorophores on solid phase resins; Implications for screening, encoding and reaction monitoring". Bioorganic & Medicinal Chemistry Letter, vol. 7, No. 12, pp. 1567-1572 (1997).
S. Dubiley et al., "Polymorphism Analysis and Gene Detection by minsequencing on an array of gel immobilized primers." Nucleic Acids Research, 1999;i-vi. vol. 27, No. 16.
S. Ebel et al. "Very Stable Mismatch Duplexes: Structural and Thermodynamic Studies on G-A Mismatches in DNA" Biochemistry 31:12083-86 (1992).

Seeman, P., et al., "Structure of Membrane Holes in Osmotic and Saponin Hemolysis"; The Journal of Cell Biology, vol. 56; pp. 519-527 (1973).
Sehgal et al. "A method for the high effieiency of water-soluble carbodiimide-mediated amidation". Analytical Biochemistry. vol. 218:87-91 (1994).
Seltsam, et al., Systematic analysis of the ABO gene diversity within exons 6 and 7 by PCR screening reveals new ABO alleles, Transfusion, vol. 43, pp. 428-439 (2003).
Sennerfors, T., et al., "Adsorption of Polyelectrolyte-Nanoparticle Systems on Silica: Influence of Ionic Strength". Journal of Colloid and Interface Science, vol. 254, pp. 222-226 (2002).
Serizawa, T., et al., "Electrostatic Adsorption of Polystyrene Nanospheres onto the Surface of an Ultrathin Polymer Film prepared by Using an Alternate Adsorption Technique". Langmuir, vol. 14, pp. 4088-4094 (1998).
Sethu, P; "Microfluidic diffusive filter for apheresis (leukopheresis)"; Lab Chip, vol. 6, No. 1, pp. 83-89 (Jan. 2006); Published electronically Nov. 11, 2005.
Seul et al., "Domain Shapes and Patterns: The Phenomenology of Modulated Phases". Science, vol. 267:476-483 (1995).
Seul et al., "Scale transformation of magnetic bubble arrays: coupling of topological disorder and polydispersity". Science, vol. 262 : 558-560 (1993).
Sgaramella, V., et al., "Total Synthesis of the Structural Gene for an Alanine Transfer RNA from Yeast. Enzymic Joining of the Chemically Synthesized Polydeoxynucleotides to form the DNA Duplex Representing Nucleotide Sequence 1 to 20". J. Mol. Biology, vol. 72, pp. 427-444 (1972).
Sham , P. et al., "Haplotype Association of Discrete and Continuous Traits Using Mixture of Regression Models", Behavior Genetics, Mar. 2004, 34(2), pp. 207-214.
Shevkoplyas, S., et al., "Biomimetic autoseparation of leukocytes from whole blood in a microfluidic device"; American Chemical Society; vol. 77, No. 3, pp. 933-937 (Feb. 1, 2005).
Shon. "Application Note—New Best Practices for Biosample Management: Moving Beyond Freezers". American Biotechnology Laboratory, vol. 23, No. 2, pp. 10-13 (2005).
Shoyer, Terrie W., et al., "A Rapid Flow Cytometry Assay for HLA Antibody Detection Using a Pooled Cell Panel Convering 14 Serological Crossreacting Groups". Transplantation, vol. 59, No. 4, pp. 626-630 (1995).
Siegel, D., "Phage display-based molecular methods in immunohematology". Transfusion, vol. 47, pp. 89S-94S (Jul. 2007 Supplement).
Simon, R. "Application of optimization methods to the hematological support of patients with disseminated malignacies", Mathematical Biosciences, vol. 25, 1975, pp. 125-138.
Skalnik et al., "A Rapid Method for Characterizing transgenic Mice", S. Biotechniques 8:34 (1990).
Skolnick et al. "Simultaneous analysis of multiple polymorphic loci using amplified sequence polymorphisms (ASPs)". Genomics, vol. 2, pp. 273-279 (1988).
Smay, J., et al., "Colloidal Inks for Directed Assembly of 3-D Peridoic Structures". Langmuir, vol. 18, pp. 5429-5437 (2002).
Smith, J. W., et al., "RED: A Red-Cell Antibody Identification Expert Module". Journal of Medical Systems, vol. 9, No. 3, pp. 121-138 (1985).
Southern E. M., "DNA Fingerprinting by hybridisation to oligonucleotide arrays". Electrophoresis, vol. 16, No. 9, pp. 1539-1542 (1995).
Southern, E. M., et al., "Analyzing and comparing nucleic acid sequences by hybridization to arrays of oligonucleotides: evaluation using experimental models". vol. 13, No. 4, pp. 1008-1017 (Aug. 1992).
St. Louis, M, et al., "The Dombrock blood group system: A Review" , Transfusion 43: 1126-1132 (2003).
Steemers, F.J. (2000) Screening unlabeled DNA targets with randomly ordered fiber-optic gene arrays. Nat. Biotechnol., 18, 91-94.
Stemmer, C., et al., "Use of Magnetic Beads for Plasma Cell-free DNA Extraction: Toward Automation of Plasma DNA Analysis for Molecular Diagnostics". Clinical Chemistry, vol. 49, No. 11, pp. 1953-1955 (2003).

(56) References Cited

OTHER PUBLICATIONS

Stevens, P. W., et al. "Imaging and Analysis of Immobilized Particle Arrays". Analytical Chemistry. vol. 75, pp. 1147-1154 (2003).
Storry et al, "Genetic Basis of blood group diversity". British Journal of Haematology, vol. 126, pp. 759-771 (2004).
Strobel E., et al., "The molecular basis of Rhesus antigen E", Transfusion 44:407-409 (2004).
Sukhishvilli, S.A. et al. "Adsorption of human serum albumin: Dependerice on molecular architecture of the oppositely charged surface" J. Chem. Phys. 110, 10153-10161 (1999).
Sun et al., "Continuous, Flow-Through Immunomagnetic Cell Sorting in a Quadrupole Field". Cytometry, vol. 33, pp. 469-475 (1998).
Suzawa et al., "Adsorption of Plasma Proteins onto Polymer Latices". Advances in Colloid and Interface Science, vol. 35, pp. 139-172 (1991).
Svitel, et al., "Combined Affinity and Rate Constant Distributions of Ligand Populations from Experimental Surface Binding Kinetics and Equilibria". Biophysical Journal, vol. 84, pp. 4062-4077 (Jun. 2003).
Syvanen, "From Gels to Chips: Minisequencing Primer Extensions for Analysis of Pont Mutations and Single Nucelotide Polymorphisms", Human Mutation 13:1-10 (1999).
Syvanen, A., et al., "Identification of Individuals by Analysis of Biallelic DNA Markers, Using PCR and Solid-Phase Minisequencing". Am. J. Hum. Genet, vol. 52, pp. 46-59 (1993).
Syvannen, A. "Toward genone-wide SNP genotyping". Nature Genetics Supplement. vol. 37: s5-s10 (2005).
Sze. MIS Diode and Charge-Coupled Device. The Physics of Semiconductors, Chapter 7, pp. 362-430 (2nd Edition) (1981).
Takeda et al. "Conformational Change of Bovine Serum Albumin by Heat Treatment", J. Protein Chemistry 8:653-659, No. 5 (1989).
Tanaka, T., et al., "Mechanical instability of gels at the phase transition", Nature, vol. 325, pp. 796-798 (1987).
Taniguchi et al. "Adsorption/desorption behavior and covalent grafting of an antibody onto cationic amino-functionalized poly(styrene-N-isoprapylacrylamide) core-shell latex particles". Colloids and Surfaces B: Biointerfaces. vol. 29: 53-65 (2003).
Tarnok et al., "Cytometric Bead Array to Measure Six Cytokines in Twenty-Five Microliters of Serum," Clinical Chemistry, (2003), vol. 49, No. 6, pp. 1000-1002.
Taylor et al., "Linked oligodeoxynucleotides show binding cooperativity and can selectively impair replication of deleted mitochondrial DNA templates", Nucleic Acids Research. vol. 29, No. 16, pp. 3404-3412 (2001).
Tobitani et al. "Heat-induced gelation of globular proteins. 1. Model for the effects of time and temperature onthe gelation time of BSA gels." Macromolecules. vol. 30:4845-4854 (1997).
Tokumasu F. et al., Development and application of quantum dots for immunocytochemistry of human erythrocytes, J. Microscopy, 2003, pp. 256-261, vol. 211, pt. 3.
Tonisson et al., "Arrayed primer extension on the DNA chip; Method and applications", Microarray Biochip Technology, Biotechniques Books, 247-262 (2000).
Tsuchihashi, Z. et al. "Progress in high throughput SNP genotyping methods", The Pharmacogenomics Journal 2:103-110 (Apr. 2002).
Trau et al., "Field-induced layering of colloidal crystal", Science, vol. 272; pp. 706-709 (1996).
Trang D.T.X. et al, "One step concentration of malarial parasite-infected red blood cells and removal of contaminating white blood cells" , Malaria Journal (2004) pp. 1-7 from //www.malariajournal.com/content/3/1/7.
Trau et al., "Nanoencapsulated microcrystalline particles for superamplified biochemical assays". Anal. Chem, vol. 74, No. 21, pp. 5480-5486. Web Release Date: Sep. 25, 2002.
Turcanu et al, "Cell Identification and isolation on the basis of cytokine secretion: A novel tool for investigating immune responses". Nature Medicine, vol. 7, No. 3, pp. 373-376 (Mar. 2001).
Tyagi et al., Molecular Beacons: Probes that Flouresce upon Hybridization, Nature Biotechnology vol. 14, pp. 303-308 (1996).

Vainrub, A., et al., "Sensitive quantitative nucleic acid detection using oligonucleotide microarrays". Journal of the American Chemical Society, vol. 125, No. 26, pp. 7798-7799, (Jun. 2003).
Van Kempen, et al., "Mean and Variance of Ratio Estimators Used in Fluorescence Ratio Imaging". Cytometry, vol. 39, pp. 300-305 (2000).
Van Zoelen, "Receptor-ligan interaction: a new method for determing binding parameters without a priori assumptions on non-specific binding". Biochem J., vol. 262, pp. 549-556 (1989).
Vasiliskov, A. V., et al., "Fabrication of Microarray of Gel-Immobilized Compounds on a Chip by Copolymerization". BioTechniques, vol. 27, pp. 592-606 (Sep. 1999).
Vaynberg et al. "Structure and extent of absorbed gelatin on acrylic latex and polystyrene collodial particles". Journal of Colloid and Interface Science. vol. 205:131-140 (1998).
Vet, J.A.M. (1999) Multiplex detection of four pathogenic retroviruses using molecular beacon. Proc. Natl. Acad. Sci. USA, 96, 6394-6399.
Vilain. "CYPs, SNPs, and Molecular Diagnosis in the Postgenomic Era". Clinical Chemistry, vol. 44, pp. 2403-2404 (1998).
Wahl et al., "Efficient transfer of large DNA fragments from agarose gels to diazobenzyloxymethyl-paper and rapid hybridization by using dextran sulfate". Proc. Natl. Acad. Sci. USA. vol. 76, No. 8: 3683-3687 (1979).
Wang, D., et al, "Large-Scale Identification, Mapping, and Genotyping of Single-Nucleotide Polymorphisms in the Human Genome". Science, vol. 280, No. 5366, pp. 1077-1082 (May 15, 1998).
Warren, J. A., "Selected Spacings During Directional Solidification of a Binary Alloy", Spatio-Temporal Patterns, Ed. P. E., Cladis and P. Palffy-Muhoray, SFI Studies in the Science of Complexity, Addison-Wesley, pp. 91-105 (1995).
Weinfeld et al., "Selective hydrolysis by exo- and endonucleases of phosphodiester bonds adjacent to an apurinic site". Nucleic Acids Research, vol. 17, No. 10: 3735-3744 (1989).
Weissenbach et al. "A Second generation linkage map of the human genome". Nature, vol. 359, pp. 794-801 (1992).
Wen, et al., "Planar Magnetic Colloidal Crystals". Physical Review Letters, vol. 85, No. 25, pp. 5464-5467 (2000).
Wiedmann, M., et al., Ligase Chain Reaction (LCR)—Overview and Applications, PCR Methods and Applications, Genome Research, vol. 3, pp. s51-s64 (1994).
Yeang et. al. Molecular classification of multiple tumor types. Bioinformatics vol. 17 Suppl. 1, pp. s316-s322 (2001).
J.F. Chapman et al., "Working Party of The BCSH: Guidelines for compatibility procedures in blood transfusion laboratories", Transfusion Medicine, vol. 14, pp. 59-73 (2004).
Yamashita et al., "Thermodynamics for the preparation of micronsized, monodispersed highly monomer absorbed polymer particles utilizing the dynamic selling method". Colloids and Surfaces, vol. 153, pp. 153-159 (1999).
Yao et al., "Molecular-beacon-based array for sensitive DNA analysis". Analytical Biochemistry, vol. 331, pp. 216-223 (2004).
Fukuda et al., "Noncontact manipulation of DNA molecule 1. Transportation of DNA molecule by dielectric force". Nippon Kikai Gakkai Ronbunshu, vol. 62: 2765-2772 (1996).
Friedli, Interaction of SWP with Bovine Serum Albumin (BSA) and Soluble Wheat Protein (SWP) (7 pages) downloaded //www.friedli.com/research/PhD/chapter5a.html.
Hermanson, Greg T., "Zero Length Cross-Linkers"; Bioconjugate Techniques; Academic Press, pp. 170-176 (1996).
Hermanson, Greg T., "Bioconjugate Techniques", Bioconjugate Techniques; Academic Press, San Diego, 430-33, (1996).
MacBeath et al., "Printing proteins as microarrays for high-throughput function determination," Science vol. 289: 1760-1763 (2000).
Tobitani et al. "Heat-induced gelation of globular proteins 2. Effect of environmental factors on single-component and mixed-protein gels," Macromolecules; vol. 30: 4855-4862 (1997).
Wittemann et al., "Interaction of Proteins with Spherical Polyelectrolyte Brushes" (Polyer Institute, University of Karisruhe, Karisruhe, Germany) Poster Oct. 2001.

* cited by examiner

MICROPARTICLES WITH ENHANCED COVALENT BINDING CAPACITY AND THEIR USES

RELATED APPLICATIONS

This invention claims priority to U.S. Provisional Application Ser. No. 60/504,716, filed Sep. 9, 2003.

FIELD OF THE INVENTION

This invention is in the field of polyelectrolyte chemistry.

BACKGROUND

As an alternative to solve many of the problems associated with diagnostic use of "spotted arrays" of oligonucleotides (the problems are outlined in "Multianalyte Molecular Analysis Using Application-Specific Random Particle Arrays," U.S. application Ser. No. 10/204,799, filed on Aug. 23, 2002; WO 01/98765) preferred arrays are formed by binding oligonucleotide probes to encoded microbead particles, including, encoded particles made of polymer resin. See U.S. patent application Ser. No. 10/271,602 "Multiplexed Analysis of Polymorphic Loci by Concurrent Interrogation and Enzyme-Mediated Detection," filed Oct. 15, 2002, and Ser. No. 10/204,799 supra. The encoded particle-probeconjugates are then assembled in a 2D array format and placed in contact with samples anticipated to contain target polynucleotides with subsequences complementary to the probes, where the target polynucleotides in the samples were previously fluorescently labeled. Binding between the probes and targets is determined by the presence of a fluorescent assay signal. Particular probes generating a positive assay signal can be determined by decoding the array.

There are several known and commercially available methods for attachment of oligonucleotide probes to microbeads. A great number of covalent immobilization schemes for oligonucleotide probes to microparticles have been devised and are available either in open literature or commercially. Traditional covalent immobilization techniques use functionalized beads (i.e, beads functionalized with reactive groups like amino, carboxyl, tosyl, aldehyde, epoxy, hydrazide and others) to link to complementary functional groups on the end of oligonucleotide probes (Maire K. Walsh, Xinwen Wang and Bart C. Weimer, Optimizing the immobilization of single-stranded DNA onto glass beads, J. Biochem. Biophys. Methods 2001; 47:221-231). Often times such binding protocols lead to improper orientation and steric hindrance problems. The hybridization performance of such covalently immobilized probes can be improved by introduction of spacer molecules (Edwin Southern, Kalim Mir and Mikhail Shchepinov; Molecular Interactions on Microarrays. Nature Genetics Supplement, 21, 1999, pp. 5-9), however, implementation is often difficult and impractical.

A practical and robust probe binding chemistry is therefore important for the optimal performance of a microbead array based assay. The chemistry must allow the probes to bind to the particles with high efficiency, in order to maintain a consistent concentration of probes on the bead surface and also the reaction must not alter the efficiency of probe-target binding. Moreover, the reaction must have minimum batch to batch variability. In one commonly used method, functionalized microparticles are coated with Neutravidin (Pierce, Rockford, Ill.), streptavidin or avidin, which are biotin binding proteins, to mediate immobilization of biotinylated probes. The avidin-biotin interaction is highly specific and one of the strongest known (with an association constant ($K_A$) of the order of $10^{15} M^{-1}$ in aqueous solutions) and provides nearly irreversible linkage between the bead surface immobilized protein and the biotinylated probe molecule. See U.S. patent application Ser. No. 10/271,602, supra. The method described below for binding probes to polyelectrolytes are preferred to these known methods, because they were demonstrated as capable of inducing attachment of greater numbers of oligonucleotides to beads.

SUMMARY

A polyelectrolyte having multiple exposed functional groups, each such group being capable of covalently bonding to a molecule, is immobilized on a surface for the purpose of bonding to a biomolecule. The biomolecule can be, for example, a nucleic acid, e.g., an amine functionalized oligonucleotide. The polyelectrolyte can include, e.g., BSA (Bovine Serum Albumin) which is bound to a functionalized surface using a covalent immobilization strategy, e.g., reaction with the surface of a tosyl-activated microparticle. Following such reaction, exposed reactive functional groups on the protein, such as amine, carboxyl, thiol, hydroxyl groups can further be utilized to covalently couple the oligonucleotide of interest using suitable chemistry.

In one embodiment, oligonucletides modified at a terminal position (the 3' or 5' terminal position) with amines (e.g., amino modified oligonucleotides) are covalently bound to BSA using an EDAC (1-ethyl-3-(3-dimethylaminopropyl) carbodiimide) reaction (see, e.g., D. Seligal et al., Analytical Biochemistry 218:87091 (1994)). The covalent reaction results in the formation of an amide bond between the amine group at the terminus of the oligonucleotide and carboxyl groups on the BSA. The reaction is illustrated in FIG. 1.

The functionalized surface can be the surface of a bead or microparticle, which can be composed of any of a number of materials, including polymers, polymer resins, glass, latex or others which can be functionalized for immobilization of a polyelectrolyte. Experiments were performed comparing BSA-coated beads with human serum albumin ("HSA"), another exemplary polyelectrolyte, and with Neutravidin as well. The results of hybridization experiments indicated that the BSA-coated beads were capable of attaching greater concentrations of oligonucleotides to the beads.

DETAILED DESCRIPTION

Example 1

Preparation of BSA-Coated Tosyl Functionalized Beads

Figure 1:
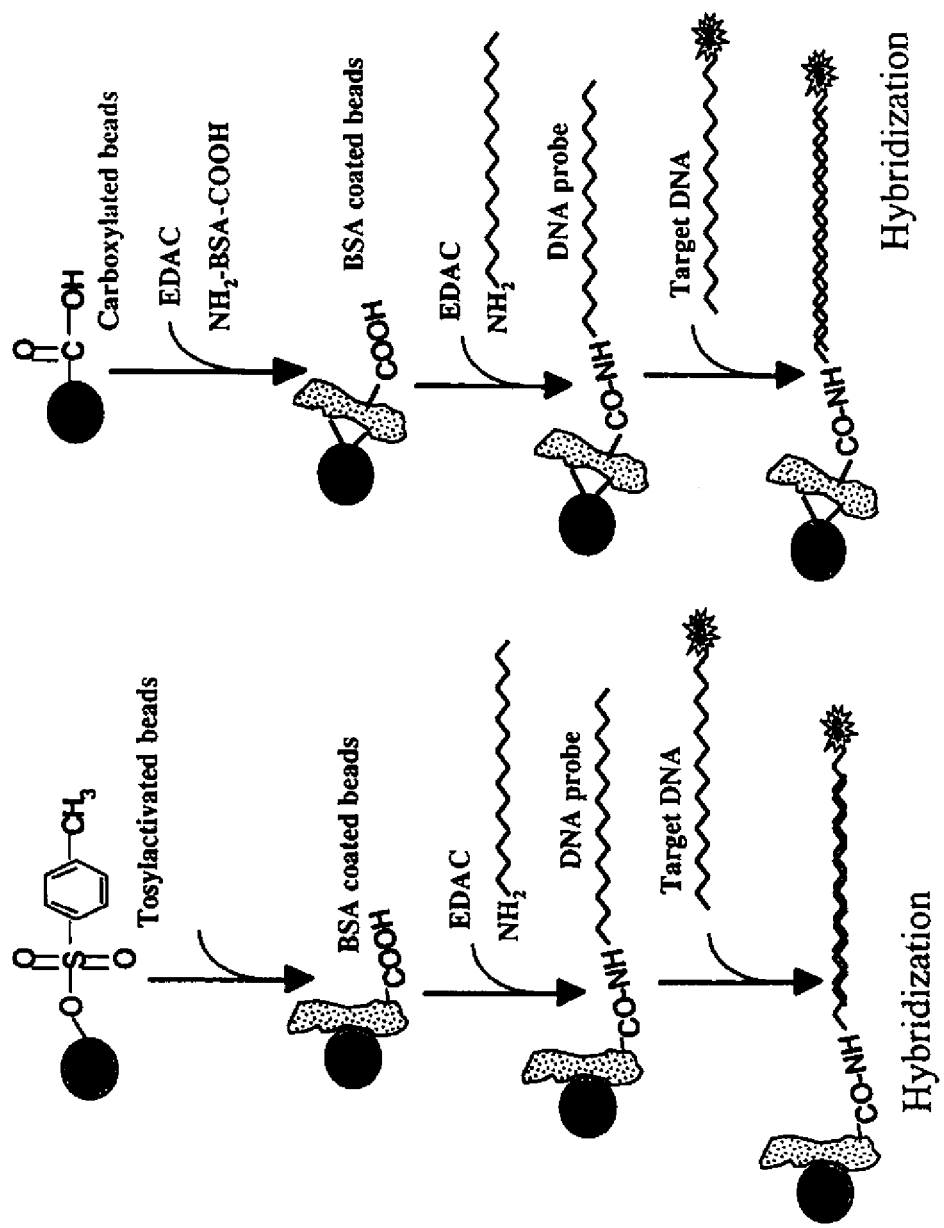
FIG. 1 illustrates the bonding of BSA to functionalized beads and the bonding of an oligonucleotide probe to the BSA using an EDAC reaction.

BSA solution at the concentration of 5 mg/mL is prepared by dissolving 50 mg of BSA in 10 mL of PBS. 2.0 mL of PBS-T is added to a 15 mL centrifuge tube. 1 mL of fluorescence colored beads at the concentration of 1% solids (10 mg) are transferred into the centrifuge tube, and mixed well by vortexing. The beads are spun down by centrifugation at 3,500 rpm for 4+/−0.5 minutes, and the supernatant is decanted. The beads are re-suspended by adding 3.0 mL of PBST into the tube, and mixed well by vortexing. The beads are again spun down by centrifugation at 3,500 rpm for 4+/−0.5 minutes, and the supernatant is discarded. 3.0 mL of BSA solution (5 mg/mL) are added to the beads, and mixed well by vortexing. The tubes are placed on a shaker in a 37° C. incubator, and the beads are allowed to react overnight with mixing at 250 rpm.

Thereafter, the beads are spun down by centrifugation at 3,500 rpm for 4 minutes, and the supernatant is discarded. The beads are then washed by adding 3.0 mL of PBS-T to the tube, and mixed on a vortex mixer. The beads are then again centrifuged at 3500 rpm for 4+/−0.5 minutes, and the supernatant is poured off. The washing and centrifuging steps are then repeated.

3.0 mL of storage buffer (0.1M PBS containing 0.1% $NaN_3$), are added, and mixed on a vortex mixer. The beads are again centrifuged at 3,500 rpm for 4+/−0.5 minutes, and the supernatant is poured off. The beads are then resuspended in 1 ml of storage buffer by vortexing. The beads are at a concentration of 1% solids (10 mg/mL), and are stored at 4-6° C.

They are ready for attachment of amine-containing biomaterials (e.g., BSA) through the EDAC reaction, as described below in Example 3.

Example 2

Preparation of BSA-Coated Carboxyl Functionalized Beads

The coupling of BSA to carboxylated particles is carried out as follows. 100 µl of carboxylated particles at a concentration of 1% solids is transferred to a 2 ml Eppendorf tube. The beads are then pelleted by centrifugation and the supernatant removed. Following this, the beads are washed 1× with 1 ml of MES (details) buffer (pH 4.5). Separately a stock solution of BSA (5 mg BSA/ml) in MES buffer and EDC (20 mg/ml) in MES buffer are prepared. 100 µl of the BSA stock solution is added to the bead pellet and the suspension mixed well by vortexing. Following this, 400 µl of the EDC stock solution is added to the bead suspension, mixed well by vortexing and allowed to react a room temperature for 1 hr with end-over-end mixing. After 1 hr incubation, 100 µl of PBS-T is added to the suspension and the beads centrifuged. The pellet is washed twice with 1 ml PBS-T by centrifugation-redispersion cycle, and the beads are finally suspended in 100 µl of storage buffer (0.1M PBS containing 0.1% sodium azide, $NaN_3$) and stored at 4-6° C.

Example 3

EDAC Reaction for Coupling of Aminated Oligonucletide Probes to BSA Beads

The coupling of aminated oligonucletide probes to the beads, prepared as in Example 1 and 2, was carried out as followsA series of 1.5 ml Eppendorf tubes were taken and labeled to identify the type of microparticle and the oligonucletide probe to be coupled. Following this, 500 µL of PBST was dispensed into each tube, followed by 100 µL of BSA coupled beads at concentration of 1% solids. The tubes were mixed well with a vortex mixer for 10 seconds. The beads were then spun down at 9500 rpm for 2+/−0.5 min, and the supernatant discarded. A 500 µL aliquot of 0.05M MES buffer (pH4.5) was added to the pellet, and mixed well by vortexing. The beads were then centrifuged at 9500 rpm for 2+/−0.5 minutes, and the supernatant discarded. A 500 ul aliquot of 0.05M of EDAC in MES buffer (prepared right before use) was added to the beads, and mixed well by vortexing. Following 10 µL each of amino modified DNA probes (e.g., probe MS-508 N25, purchased from Integrated DNA Technologies, Inc., Coralville Iowa) was added at a concentration of 100 µM to each of the tubes containing the bead suspensions, and mixed well. The reaction is allowed to proceed for 1 hour at room temperature (20-25° C.) with end-over-end mixing.

After the incubation, 100 µL of PBS-T is added to each tube, and mixed by vortexing. The beads are then spun down in a centrifuge at 9500 rpm for 2+/−0.5 minutes, and the supernatant discarded. The beads are then washed twice with 500 ul PBS-T using the centrifugation redispersion cycle.

The beads are resuspended in 100 µL of PBST to bring the final concentration to 1% solids, and stored at 4-6° C. for further use.

Figure 2:
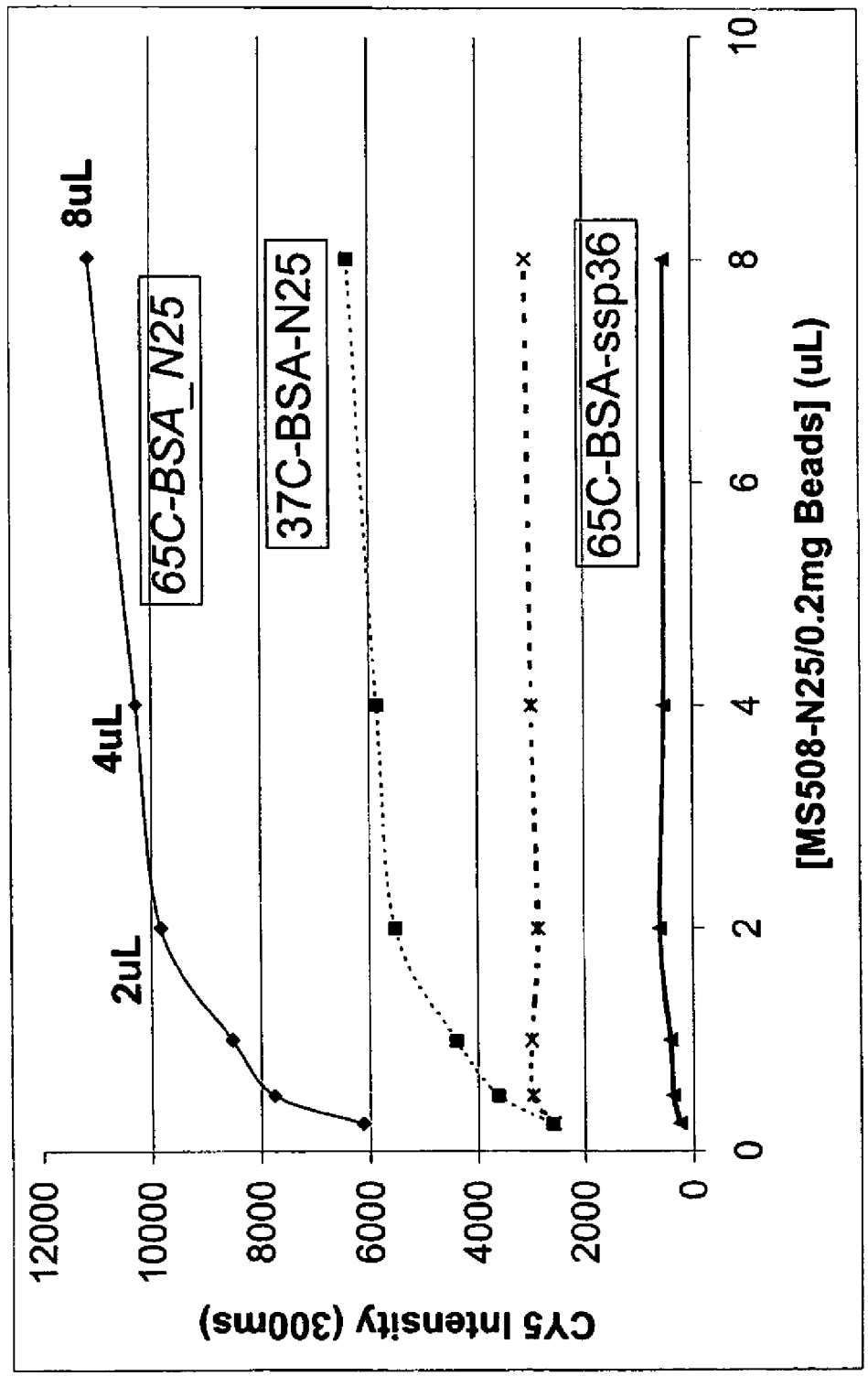
FIG. 2 shows the hybridization signals from oligo-functionalized BSA coupled beads as a function of the amount of added aminated probe for coupling. A perfectly matching probe was attached to two sets of BSA-coupled beads. BSA was coupled to the first set of beads at 65° C. and to a second set at 37° C. A much higher hybridization efficiency was noted (higher signal) on the first set of beads to which BSA was coupled at 65° C. A third set of beads coupled with BSA at 65° C. and functionalized with a mismatched negative control probe shows negligible hybridization, thus indicating that the enhanced signal is not a result of increased non-specific binding.

The hybridization performance (see Example 4 for protocol) of oligonucleotide functionalized particles as a function of added amount of oligo (0.25, 0.5, 1, 2, 4, 8 ul of 100 uM/200 ug particles) is shown in FIG. 2. The amount described above 10 ul of 100 uM/1 mg thus represents a saturation concentration. Also, the beads with BSA coupled at higher temperature show improved hybridization performance as described in detail later.

Example 4

Hybridization Assay Using Oligonucletide Functionalized Beads

1. Bead mixtures are assembled on 8 different chips. Stock fluorescently labeled DNA target solution (MS508-90mer-CY5) is prepared in hybridization buffer (1×TMAC. Eight different serial dilutions are prepared from the stock target solution. 20 µl of each of the serially diluted target solutions are then added to the eight separate chips.
2. A slide, containing the chips, is placed in a hybridization heater/shaker, and incubated at 55° C. for 20 minutes at 100 rpm.
3. The slide is removed and cooled to room temperature, and the hybridization solution is removed with the transfer pipette.
4. 20 µl of 1×TMAC is added to each chip, and the chip is washed by pipetting the solution 8 to 10 times.
5. The washing solution is removed and 5 ml of mounting solution (1×TMAC) is added to each chip, and the assay signal (CY5) is read under a fluorescent microscope using a coverslip.
6. A titration curve is plotted of the hybridization signal (CY5) vs DNA probe concentration.

Figure 3:
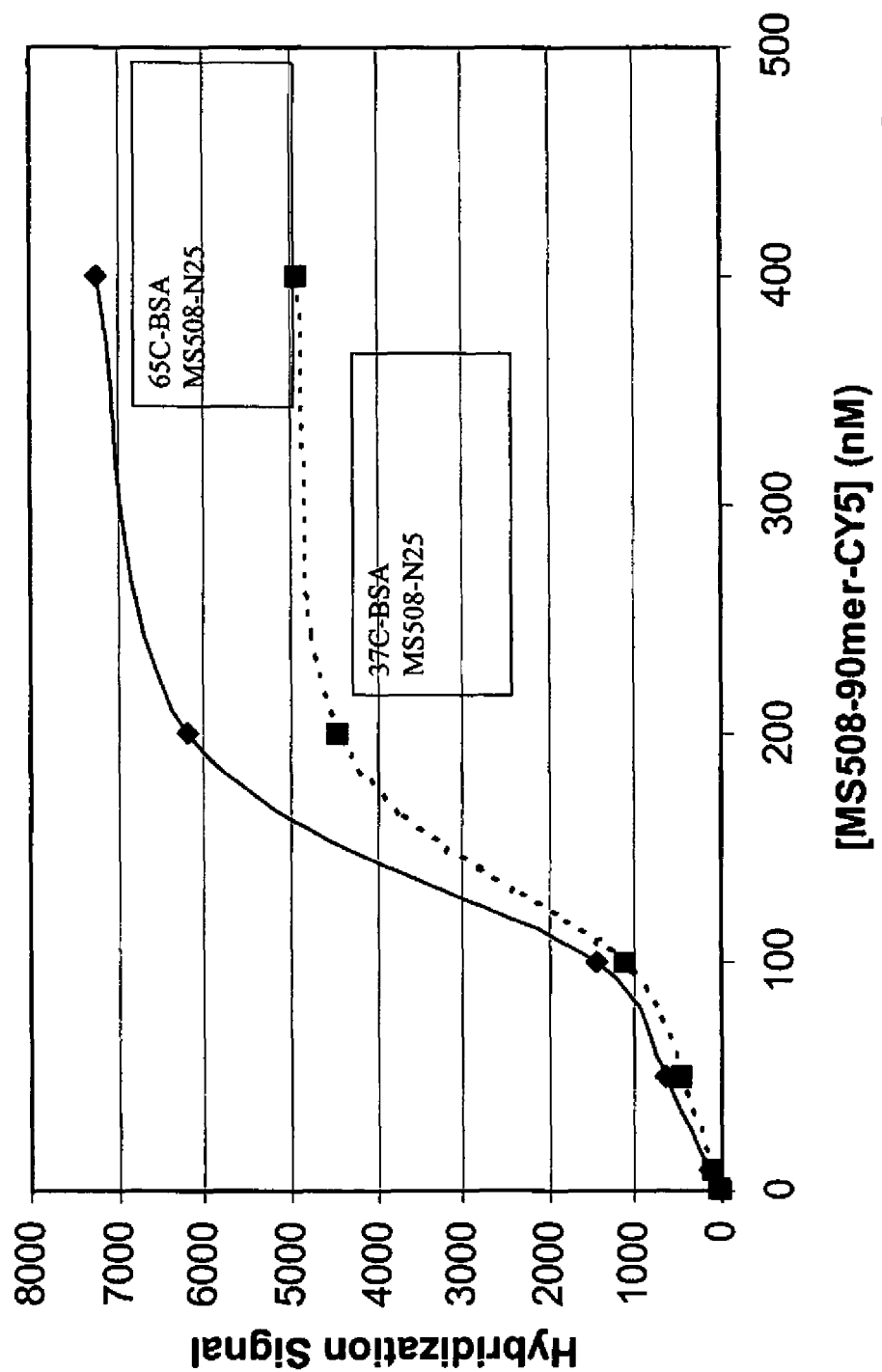
FIG. 3 shows titration results of BSA coupled beads. As in FIG. 2, efficiency of hybridization is greater for the beads coupled with BSA at a higher temperature than at a lower temperature, as demonstrated by the difference in hybridization signal from a target placed in contact with an oligonucleotide probe bound to BSA-coupled beads where BSA was coupled to one set of beads at 37° C., and where BSA was coupled to another set of beads at 65° C. (see Example 4)

Example of titration curves are shown in FIG. 3.

Example 5

Experiments were conducted to compare the effect of adding EDAC to the bead-probe suspension twice (EDAC is known to hydrolyze very quickly at acidic pH) to assess whether this leads to an enhanced binding of probes to the BSA layer. First, the probe MS-508-N25 was coupled to BSA-coated beads under each of the following condition: (10 µl 100 µM probe/100 µl 1% beads). One-half of the beads were removed from the 1× tube after one hour of reaction time, and fresh EDAC was added, and then the reaction proceeded in this tube for one additional hour. The whole process was then repeated for the non-matching probe SSP 36. Each set of beads were pooled with the non-specific beads and assembled on a chip, and then all sets were placed in contact with target MS 508-40mer-Cy5 under hybridizing conditions. Results were then recorded, and are summarized below in Table II. 2×EDAC addition provided higher hybridization signals.

TABLE II

| Probe Concentration | Model Assay Cy5 Signal | CV | Non-specific Cy5 Signal | CV |
|---|---|---|---|---|
| 1X EDAC | 536.1 | 0.17 | 79.9 | 0.26 |
| 2X extra EDAC | 732.9 | 0.17 | 53.3 | 0.19 |

Example 6

BSA Coupling to Tosyl Activated Beads at Different Temperatures and Their Hybridization Characteristics 2.0 mL of PBST was added to each of five 15 mL centrifuge tubes and 1 mL of fluorescence colored beads, at the concentration of 1% solids (10 mg), was added to each tube, and then the beads were mixed by vortexing. The beads were spun down by centrifugation at 3,500 rpm for 4+/−0.5 minutes, and the supernatant was decanted. The beads were then resuspended in 3.0 mL of PBST, mixed well by vortexing, and again spun down by centrifugation at 3,500 rpm for 4+/−0.5 minutes. The supernatant was then poured off.

2 mL of PBS (pH7.2) and 1 mL of BSA solution (50 mg/mL in PBS) was added to each tube, and mixed well by vortexing. The ambient temperature in an incubator for each of the tubes was set as follows: tube A—22° C., tube B—37° C., tube—50° C., tube D—65° C. and tube E—75° C., and the beads were allowed to react with BSA for 14 hours at the designated temperature, with end-over-end mixing. The tubes were then cooled to room temperature, and the beads spun down by centrifugation at 3,500 rpm for 4 minutes, and the supernatant poured off. The beads were then washed by adding 3.0 mL of PBST to the tube, mixed on a vortex mixer, and spun down at 3500 rpm for 4+/−0.5 minutes. The supernatant was poured off.

1 mL of storage buffer (PBS containing 0.1% $NaN_3$) was added, and the tubes were mixed on a vortex mixer. The bead concentration was 1% solids (10 mg/mL). The BSA coupled beads were stored at 4-6° C.

The 25-mer MS-508 N25 biotinylated oligonucleotide probe was conjugated to each set of beads through the EDAC coupling method described above. Each set of beads was then contacted with a fixed concentration of labeled target (a 90-mer oligonucleotide labeled with Cy-5) for the probe under hybridizing conditions. The quantity of label on the beads correlates with the probe concentration on the beads.

Figure 4:
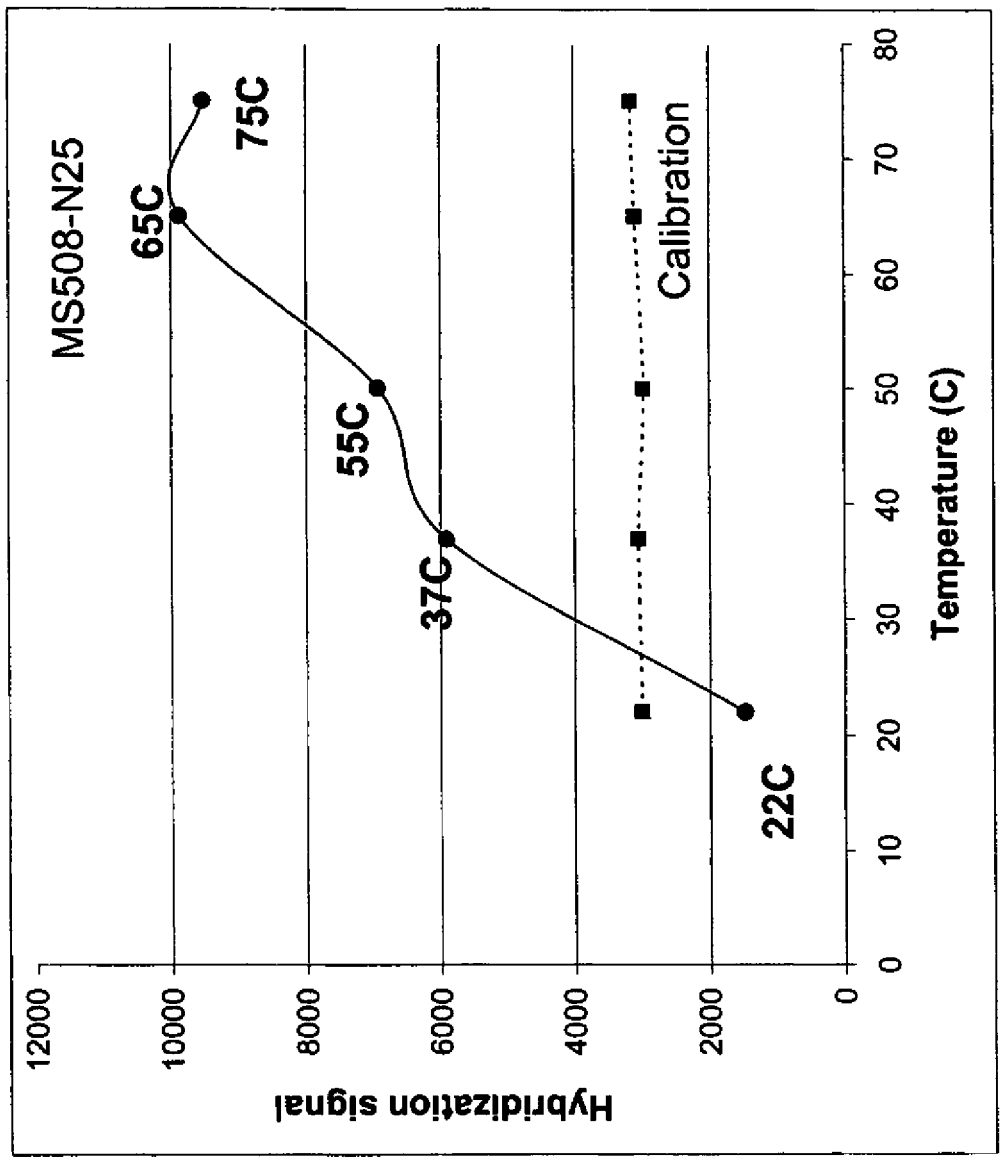
FIG. 4 indicates a differences in coupling efficiency of BSA to tosyl functionalized beads at different temperatures, as determined using a hybridization assay, where oligonucleotide probes are bound to the BSA immobilized on the beads and then reacted with a complementary fluorescently labeled target. (see Example 6)

As shown in FIG. 4, the beads which were coupled to BSA at higher temperatures displayed more target binding to the oligonucleotide probes displayed on the bead surface. This indicates that there is a greater concentration of probes at the surface of such beads, which may be because at 65° C., BSA denatures and opens up, presenting more available binding sites to the probes.

Example 7

Figure 5:
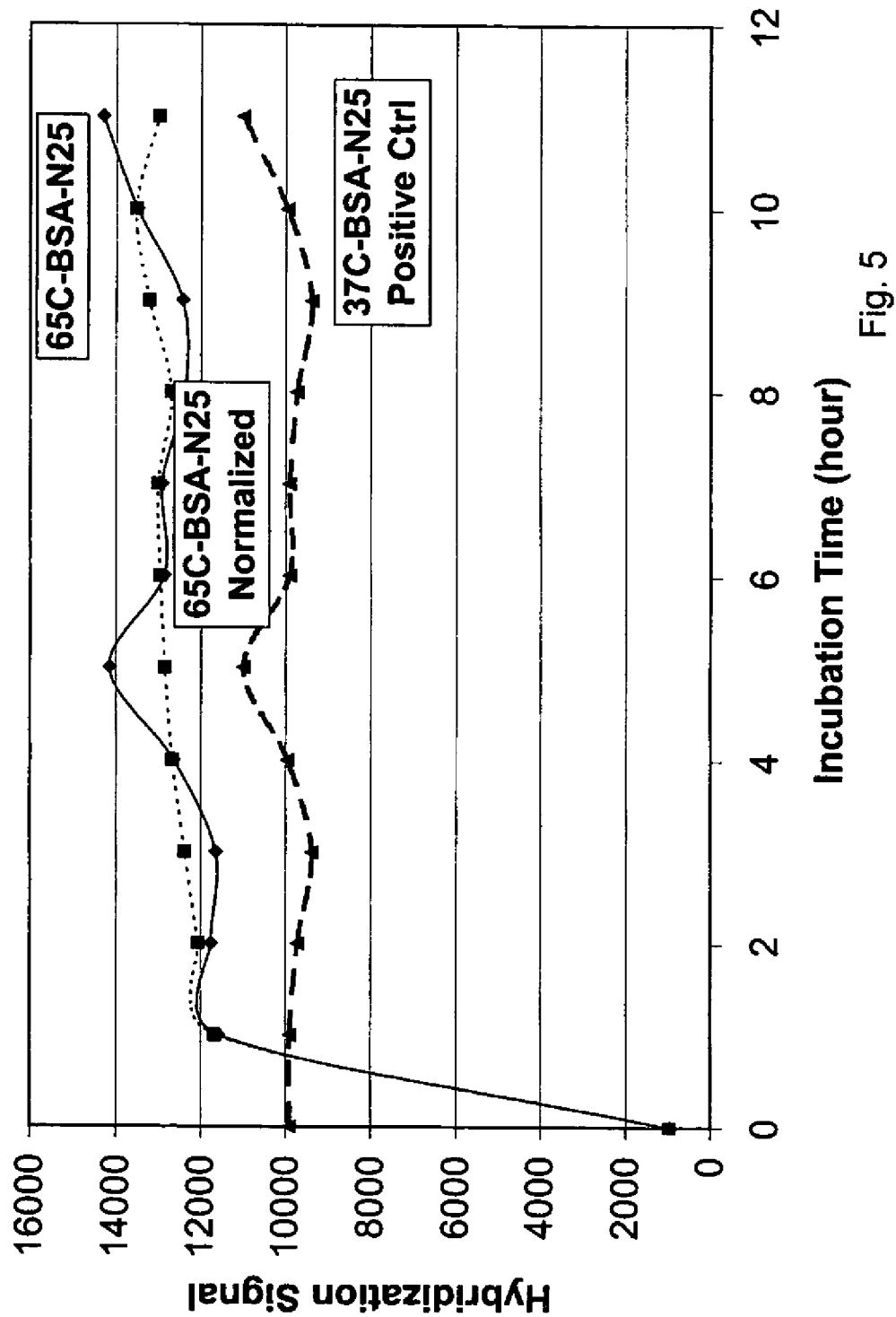
FIG. 5 indicates that for incubation at 65° C. or higher for about 1 hour, for the coupling reaction of BSA to tosyl activated beads, the binding efficiency of BSA to the bead surface is not affected, as demonstrated by the difference in hybridization signal from a target placed in contact with an oligonucleotide probe bound to BSA-coupled beads. (see Example 7)

Comparison of Varying Incubation Time for BSA Coupling to Tosyl Functionalized Particles An Experiment was conducted to study the time course of BSA coupling reaction on tosylated particles. Following the same protocol as in Examples 1 and 5 above, 12 separate tubes, each containing a BSA-tosyl particle reaction mixture, were incubated at 65° C. in an oven, and one control tube was incubated at 37° C. Each tube was taken out after a predetermined incubation period, washed and then coupled with a oligonucleotide probe (including one control probe) following method outlined in Example 3. Following this, a hybridization reaction was performed and the assay intensity was recorded (see Example 4). The results are shown in FIG. 5 which illustrates that the BSA coupling reaction is essentially complete in less than one hour.

Example 8

Comparison with Conventional Biotin-Avidin Oligonucleotide Coupling and NeutrAvidin Coating Chemistry An experiment was carried out to compare the capture and hybridization efficiency of oligo-conjugated, BSA-functionalized beads with biotinylated oligo-conjugated NeutrAvidin bead. The proteins were coupled to the bead surface at 37° C. using a protocol as outlined in Example 1. Following this, biotinylated (and also aminated) oligos were conjugated to particles (as in Example 3) and a hybridization assay was carried out with a cognate target.

Two differently encoded but otherwise identical BSA coated particles were taken and a matching probe was bound to one group and a non-matching probe was bound to the other group. Similarly two other NeutrAvidin-functionalized beads were taken and bound to matched and mismatched biotinylated probes.

Figure 6A:
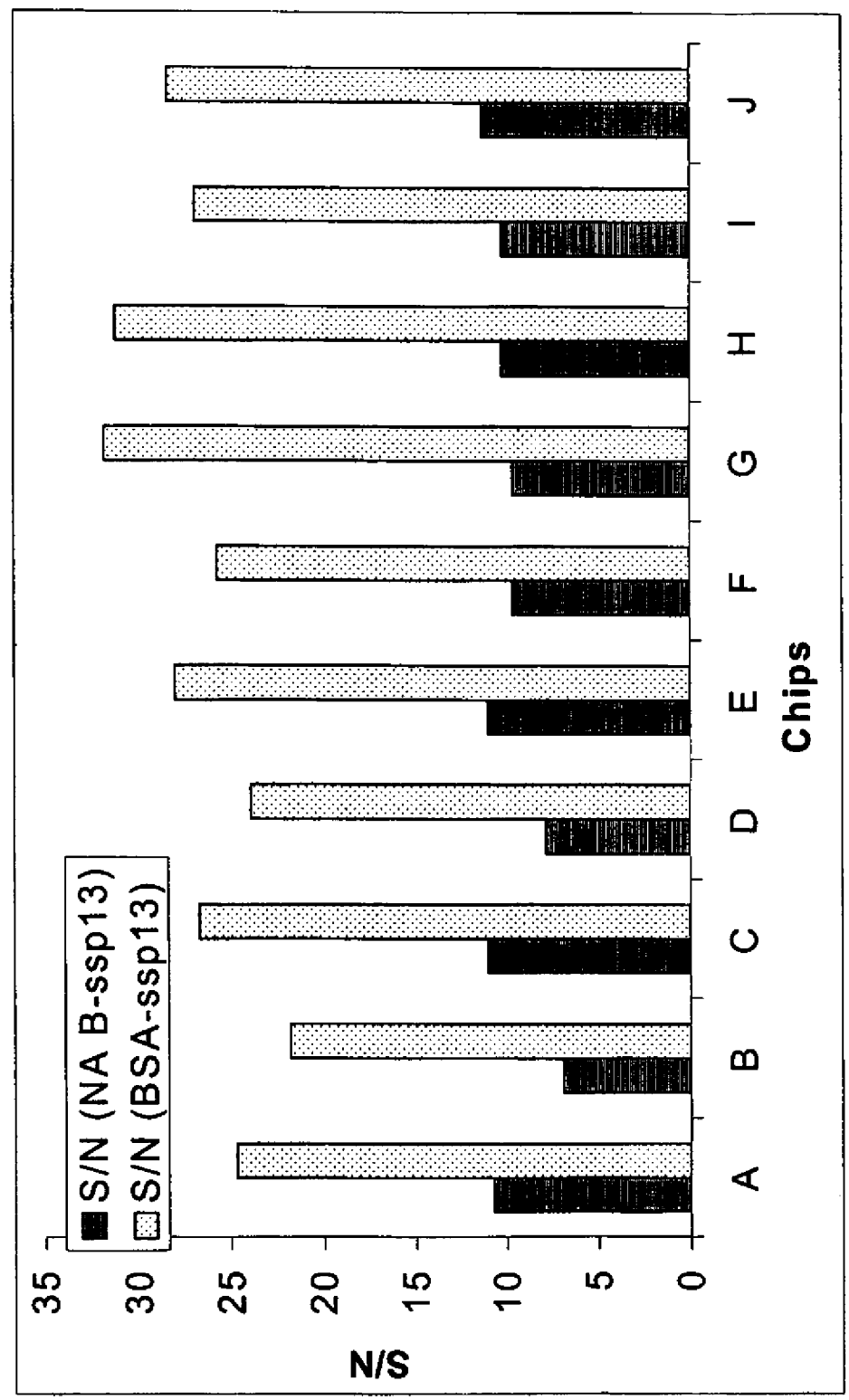
FIG. 6A shows that BSA coated tosyl functionalized beads give a more uniform and stronger hybridization signal, following bonding of probes and hybridization with a target, than a Neutravidin-coated tosyl bead. (see Example 8)
Figure 6B:
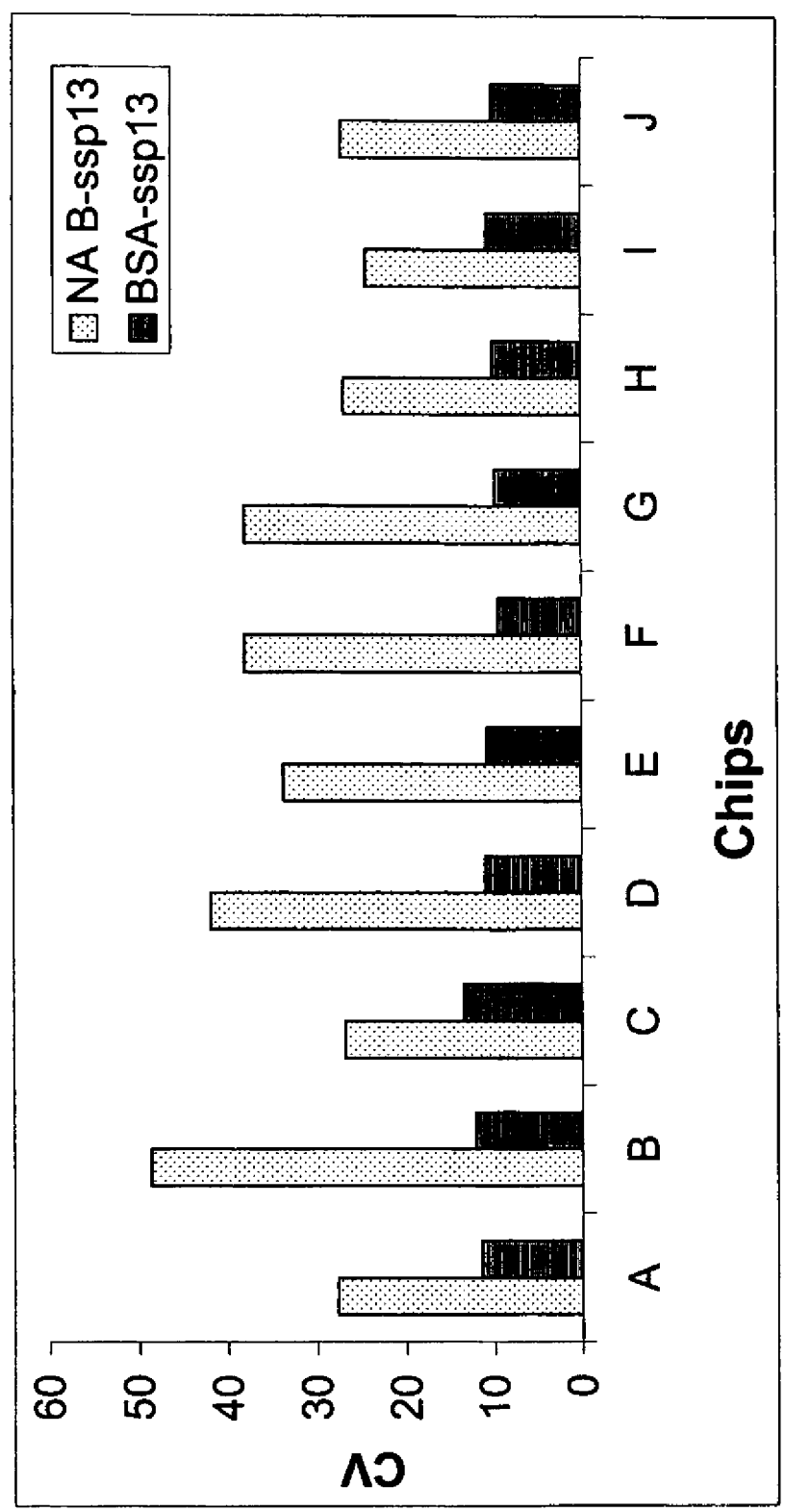
FIG. 6B shows the coefficient of variation of the signals in FIG. 6A.

The results of the assay are shown in FIGS. 6A and 6B. It is evident that BSA coating provides a more uniform (lower CV) and higher signal to noise ratio (the hybridization intensity on the mismatched probe was considered as noise) than achieved when using the NeutrAvidin capture chemistry.

Example 9

Comparison with HSA Coating

Figure 7:
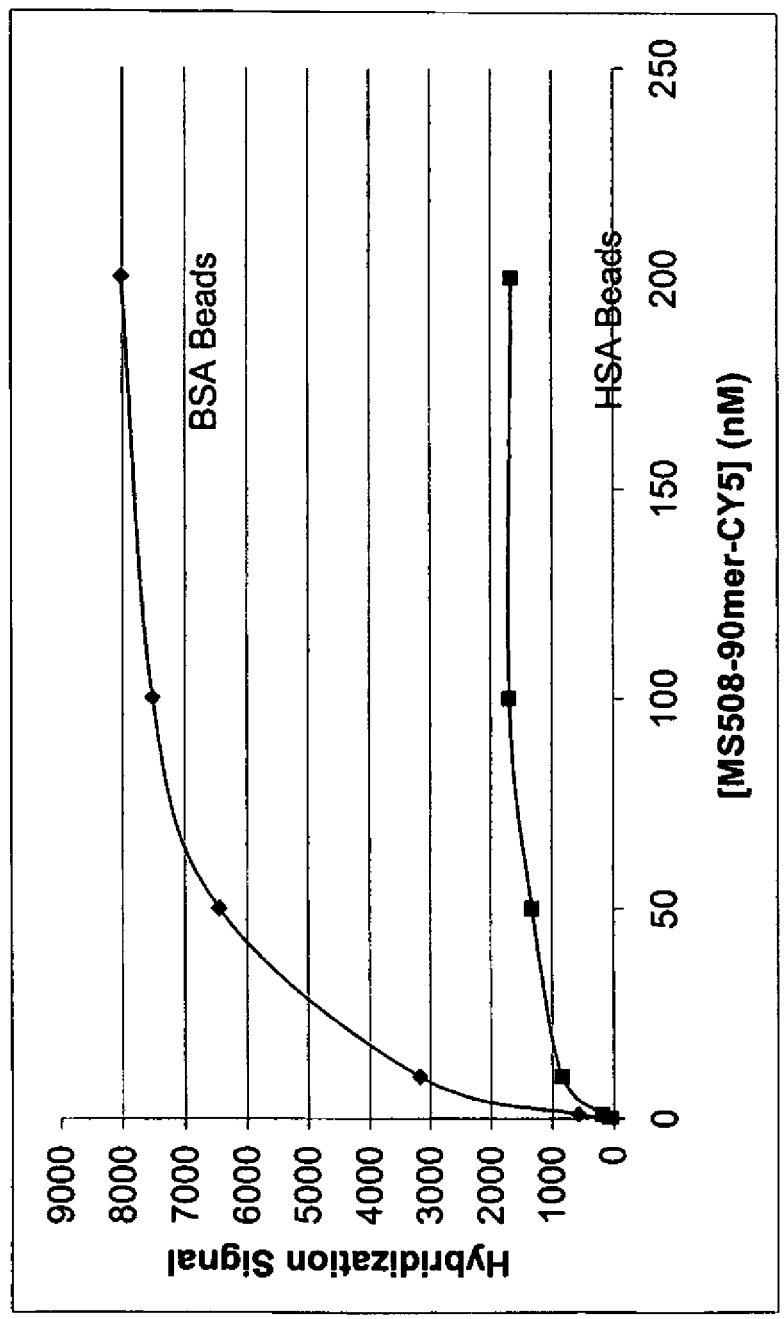
FIG. 7 shows a significant difference in hybridization when HSA, rather than BSA, is the polyelectrolyte coated on tosyl functionalized beads, where oligonucleotide probes are bound, respectively, to BSA or HSA immobilized on beads, and then reacted with a complementary fluorescently labeled target.

HSA (Human Serum Albumin) was coupled under identical conditions to those used for BSA coupling to tosyl-functionalized particles. The HSA functionalized particles were then coupled with oligonucleotide probes and hybridized (titrated) to a fluorescently labeled model DNA target (as in Example 4). The results are shown in FIG. 7. It indicates that the HSA coating is not as effective as the BSA coating for binding the oligonucleotide probes notwithstanding the fact that, like BSA, HSA has many functional carboxyl groups available for binding to the oligonucleotide probes.

Example 10

Batch to Batch Variation of BSA Coupling

Three batches of beads of 10 mg/each were separately coupled with BSA at 65° C. for 14 hours, where the BSA-bead ratio was 5 (W/W, mg/mg). The reaction volume for coupling was 3 mL. One batch of beads was coupled to BSA at 37° C. for use as a control. The coupling efficiency was determined based on signal intensity for hybridization of DNA probes coupled to the beads to cognate targets. The hybridization was done at 55° C. for 20 minutes in 1×TMAC, and the target was MS508-90mer-CY5 at a concentration of 400 nM. The integration time for assay read-out is 200 ms. The results are shown in Table I.

TABLE I

| Batch | CY5 Intensity (100 ms) |
|---|---|
| 1 | 6864 |
| 2 | 6515 |
| 3 | 6431 |
| Control | 3964 |

The 65° C. batches had a consistently higher intensity than the batch coupled at 37° C. and also the batch to batch variability was small.

The terms, expressions and examples hereinabove are exemplary only, and not limiting, and the invention is defined only in the claims which follow, and includes all equivalents of the subject matter of the claims.

What is claimed is:

1. A product comprising:
   a. A microparticle; and
   b. Bovine Serum Albumin (BSA) covalently attached to said microparticle, wherein said BSA comprises activated binding sites capable of forming a covalent bond with a primary amino group.

2. The product of claim 1, wherein said microparticle comprises a carboxy-functionalized surface.

3. The product of claim 1, wherein said microparticle comprises a tosyl-activated surface.

* * * * *